US 8,172,827 B2

(12) United States Patent
Deem et al.

(10) Patent No.: US 8,172,827 B2
(45) Date of Patent: May 8, 2012

(54) APPARATUS FOR TREATING ASTHMA USING NEUROTOXIN

(75) Inventors: Mark E. Deem, Mountain View, CA (US); Hanson S. Gifford, III, Woodside, CA (US)

(73) Assignee: Innovative Pulmonary Solutions, Inc., Bellevue, WA (US)

( * ) Notice: Subject to any disclaimer, the term of this patent is extended or adjusted under 35 U.S.C. 154(b) by 761 days.

(21) Appl. No.: 11/445,644

(22) Filed: Jun. 1, 2006

(65) Prior Publication Data

US 2006/0222667 A1  Oct. 5, 2006

Related U.S. Application Data

(63) Continuation of application No. 10/437,882, filed on May 13, 2003, now abandoned.

(51) Int. Cl.
*A61M 31/00* (2006.01)
*A62B 9/00* (2006.01)
(52) U.S. Cl. ...... 604/506; 604/500; 604/48; 128/200.24
(58) Field of Classification Search ............... 604/93.01, 604/164.01, 164.11, 164.12, 264, 272, 500, 604/506–509; 128/200.26, 898; 606/1–44, 606/45–47, 180, 183
See application file for complete search history.

(56) References Cited

U.S. PATENT DOCUMENTS

| 1,695,107 | A |   | 12/1928 | Kahl |   |
|---|---|---|---|---|---|
| 3,918,449 | A | * | 11/1975 | Pistor | 604/47 |
| 3,946,745 | A |   | 3/1976 | Hsiang-Lai et al. | 128/421 |
| 3,949,743 | A |   | 4/1976 | Shanbrom | 128/173.1 |
| 4,305,402 | A |   | 12/1981 | Katims | 128/741 |
| 4,351,330 | A |   | 9/1982 | Scarberry | 128/207.15 |
| 4,503,863 | A |   | 3/1985 | Katims | 128/741 |
| 4,565,200 | A |   | 1/1986 | Cosman | 128/642 |
| 4,643,186 | A |   | 2/1987 | Rosen et al. | 128/303.1 |
| 4,649,935 | A |   | 3/1987 | Charmillot et al. | 128/783 |
| 4,658,836 | A |   | 4/1987 | Turner | 128/804 |
| 4,765,322 | A |   | 8/1988 | Charmillot et al. | 128/783 |
| 4,767,402 | A |   | 8/1988 | Kost et al. |   |
| 4,808,164 | A |   | 2/1989 | Hess | 604/95 |
| 4,881,542 | A |   | 11/1989 | Schmidt et al. | 128/207.14 |

(Continued)

FOREIGN PATENT DOCUMENTS

CA        2419228        8/2004

(Continued)

OTHER PUBLICATIONS

Blindt et al., "Development of a New Biodegradable Intravascular Polymer Stent with Simultaneous Incorporation of Bioactive Substances", The International Journal of Artificial Organs, 1998, pp. 843-853, vol. 22-No. 12.

(Continued)

*Primary Examiner* — Justine Yu
*Assistant Examiner* — Rachel Young
(74) *Attorney, Agent, or Firm* — Seed IP Law Group PLLC

(57) ABSTRACT

Apparatus for providing intrabronchial delivery of neurotoxins to control the effects of asthma comprises a shaft having proximal and distal ends and a neurotoxin applicator assembly disposed on the distal end. The neurotoxin applicator assembly comprises a deployable needle assembly, a rotating needle assembly, and a needle-less injection assembly or a nebulizer assembly.

22 Claims, 5 Drawing Sheets

U.S. PATENT DOCUMENTS

| | | | |
|---|---|---|---|
| 4,904,472 A | 2/1990 | Belardinelli et al. | 514/263 |
| 4,945,910 A | 8/1990 | Budyko et al. | 128/421 |
| 4,955,377 A | 9/1990 | Lennox et al. | 128/401 |
| 4,989,604 A | 2/1991 | Fang | 128/421 |
| 4,992,474 A | 2/1991 | Skidmore et al. | 514/653 |
| 5,007,908 A | 4/1991 | Rydell | 606/47 |
| 5,054,486 A | 10/1991 | Yamada | 128/421 |
| 5,056,529 A * | 10/1991 | de Groot | 600/567 |
| 5,057,107 A | 10/1991 | Parins et al. | 606/48 |
| 5,107,835 A | 4/1992 | Thomas | 128/419 R |
| 5,109,846 A | 5/1992 | Thomas | 128/421 |
| 5,117,828 A | 6/1992 | Metzger et al. | 128/642 |
| 5,123,413 A | 6/1992 | Hasegawa et al. | 128/419 G |
| 5,126,375 A | 6/1992 | Skidmore et al. | 514/651 |
| 5,135,480 A | 8/1992 | Bannon et al. | 604/20 |
| 5,139,029 A * | 8/1992 | Fishman et al. | 600/556 |
| 5,151,100 A | 9/1992 | Abele et al. | 606/28 |
| 5,152,286 A | 10/1992 | Sitko et al. | 128/422 |
| 5,190,540 A | 3/1993 | Lee | 606/28 |
| 5,225,445 A | 7/1993 | Skidmore et al. | 514/651 |
| 5,286,254 A | 2/1994 | Shapland et al. | |
| 5,324,255 A | 6/1994 | Passafaro et al. | 604/22 |
| 5,344,398 A | 9/1994 | Hara | 604/96 |
| 5,348,554 A | 9/1994 | Imran et al. | 606/41 |
| 5,370,675 A | 12/1994 | Edwards et al. | 607/101 |
| 5,372,603 A | 12/1994 | Acker et al. | 606/194 |
| 5,405,362 A | 4/1995 | Kramer et al. | 607/5 |
| 5,405,366 A | 4/1995 | Fox et al. | 607/50 |
| 5,454,840 A | 10/1995 | Krakovsky et al. | 607/39 |
| 5,478,578 A | 12/1995 | Arnold et al. | 424/499 |
| 5,496,271 A | 3/1996 | Burton et al. | 604/54 |
| 5,496,304 A * | 3/1996 | Chasan | 606/1 |
| 5,540,730 A | 7/1996 | Terry, Jr. et al. | 607/40 |
| 5,562,608 A | 10/1996 | Sekins et al. | 604/20 |
| 5,571,088 A | 11/1996 | Lennox et al. | 604/96 |
| 5,620,463 A | 4/1997 | Drolet | 607/3 |
| 5,658,278 A | 8/1997 | Imran et al. | 606/41 |
| 5,658,322 A | 8/1997 | Fleming | 607/50 |
| 5,658,549 A | 8/1997 | Akehurst et al. | 424/45 |
| 5,660,175 A | 8/1997 | Dayal | 128/207.15 |
| 5,674,472 A | 10/1997 | Akehurst et al. | 424/45 |
| 5,690,692 A | 11/1997 | Fleming | 607/50 |
| 5,707,400 A | 1/1998 | Terry, Jr. et al. | 607/44 |
| 5,766,605 A | 6/1998 | Sanders et al. | |
| 5,800,486 A | 9/1998 | Thome et al. | 607/105 |
| 5,814,078 A | 9/1998 | Zhou et al. | 607/1 |
| 5,817,073 A * | 10/1998 | Krespi | 604/272 |
| 5,820,589 A | 10/1998 | Torgerson et al. | |
| 5,843,088 A * | 12/1998 | Barra et al. | 606/108 |
| 5,849,026 A | 12/1998 | Zhou et al. | 607/90 |
| 5,860,974 A | 1/1999 | Abele | 606/41 |
| 5,871,483 A | 2/1999 | Jackson et al. | 606/41 |
| 5,891,027 A | 4/1999 | Tu et al. | 600/374 |
| 5,891,182 A | 4/1999 | Fleming | 607/50 |
| 5,902,268 A | 5/1999 | Saab | 604/96 |
| 5,911,218 A | 6/1999 | DiMarco | 128/200.24 |
| 5,931,806 A | 8/1999 | Shimada | 604/24 |
| 5,956,501 A | 9/1999 | Brown | 395/500.32 |
| 5,957,919 A | 9/1999 | Laufer | 606/28 |
| 5,964,223 A | 10/1999 | Baran | |
| 5,972,026 A | 10/1999 | Laufer et al. | 607/96 |
| 5,989,545 A * | 11/1999 | Foster et al. | 424/183.1 |
| 5,995,873 A | 11/1999 | Rhodes | 607/46 |
| 6,006,134 A | 12/1999 | Hill et al. | 607/9 |
| 6,016,437 A | 1/2000 | Tu et al. | 600/374 |
| 6,033,397 A | 3/2000 | Laufer et al. | 606/27 |
| 6,043,273 A | 3/2000 | Duhaylongsod | 514/478 |
| 6,060,454 A | 5/2000 | Duhaylongsod | 514/26 |
| 6,063,768 A | 5/2000 | First | |
| 6,083,249 A | 7/2000 | Familoni | 607/40 |
| 6,083,255 A | 7/2000 | Laufer et al. | 607/96 |
| 6,087,394 A | 7/2000 | Duhaylongsod | 514/478 |
| 6,097,985 A | 8/2000 | Kasevich et al. | 607/102 |
| 6,101,412 A | 8/2000 | Duhaylongsod | 607/2 |
| 6,125,301 A | 9/2000 | Capel | 607/74 |
| 6,127,410 A | 10/2000 | Duhaylongsod | 514/478 |
| 6,129,726 A | 10/2000 | Edwards et al. | 606/41 |
| 6,139,845 A | 10/2000 | Donovan | |
| 6,141,589 A | 10/2000 | Duhaylongsod | 607/10 |
| 6,143,277 A | 11/2000 | Ashurst et al. | 424/45 |
| 6,174,323 B1 | 1/2001 | Biggs et al. | 606/232 |
| 6,198,970 B1 | 3/2001 | Freed et al. | 607/42 |
| 6,200,333 B1 | 3/2001 | Laufer | 607/96 |
| 6,203,562 B1 | 3/2001 | Ohkubo | 606/204 |
| 6,212,432 B1 | 4/2001 | Matsuura | 607/76 |
| 6,230,052 B1 | 5/2001 | Wolff et al. | 607/2 |
| 6,251,368 B1 | 6/2001 | Akehurst et al. | 424/45 |
| 6,253,762 B1 | 7/2001 | Britto | 128/200.14 |
| 6,254,598 B1 | 7/2001 | Edwards et al. | 606/41 |
| 6,254,599 B1 | 7/2001 | Lesh et al. | 606/41 |
| 6,258,083 B1 | 7/2001 | Daniel et al. | 606/15 |
| 6,258,087 B1 | 7/2001 | Edwards et al. | 606/41 |
| 6,265,379 B1 | 7/2001 | Donovan | |
| 6,273,886 B1 | 8/2001 | Edwards et al. | 606/34 |
| 6,273,907 B1 | 8/2001 | Laufer | 607/96 |
| 6,283,988 B1 | 9/2001 | Laufer et al. | 607/96 |
| 6,283,989 B1 | 9/2001 | Laufer et al. | 607/96 |
| 6,299,633 B1 | 10/2001 | Laufer | 607/96 |
| 6,302,870 B1 * | 10/2001 | Jacobsen et al. | 604/272 |
| 6,303,509 B1 | 10/2001 | Chen et al. | 438/706 |
| 6,306,423 B1 | 10/2001 | Donovan et al. | |
| 6,315,173 B1 | 11/2001 | Di Giovanni et al. | 222/402.2 |
| 6,325,798 B1 | 12/2001 | Edwards et al. | 606/41 |
| 6,327,503 B1 | 12/2001 | Familoni | 607/40 |
| 6,341,236 B1 | 1/2002 | Osorio et al. | 607/45 |
| 6,356,786 B1 | 3/2002 | Rezai et al. | 607/45 |
| 6,356,787 B1 | 3/2002 | Rezai et al. | 607/45 |
| 6,358,926 B2 | 3/2002 | Donovan | |
| 6,361,554 B1 | 3/2002 | Brisken | |
| 6,363,937 B1 | 4/2002 | Hovda et al. | 128/898 |
| 6,366,814 B1 | 4/2002 | Boveja et al. | 607/45 |
| 6,383,509 B1 | 5/2002 | Donovan et al. | |
| 6,402,744 B2 | 6/2002 | Edwards et al. | 606/41 |
| 6,405,732 B1 | 6/2002 | Edwards et al. | 128/898 |
| 6,411,852 B1 | 6/2002 | Danek et al. | 607/42 |
| 6,414,018 B1 | 7/2002 | Duhaylongsod | 514/478 |
| 6,423,058 B1 | 7/2002 | Edwards et al. | 606/41 |
| 6,424,864 B1 | 7/2002 | Matsuura | 607/3 |
| 6,425,887 B1 * | 7/2002 | McGuckin et al. | 604/272 |
| 6,432,092 B2 * | 8/2002 | Miller | 604/272 |
| 6,438,423 B1 | 8/2002 | Rezai et al. | 607/46 |
| 6,440,128 B1 | 8/2002 | Edwards et al. | 606/41 |
| 6,447,505 B2 | 9/2002 | McGovern et al. | 606/41 |
| 6,447,785 B1 | 9/2002 | Donovan | 424/239.1 |
| 6,448,231 B2 | 9/2002 | Graham | |
| 6,464,680 B1 | 10/2002 | Brisken et al. | |
| 6,464,697 B1 | 10/2002 | Edwards et al. | 606/41 |
| 6,475,160 B1 * | 11/2002 | Sher | 600/556 |
| 6,485,416 B1 | 11/2002 | Platt et al. | 600/300 |
| 6,488,673 B1 | 12/2002 | Laufer et al. | 604/516 |
| 6,491,710 B2 | 12/2002 | Satake | 606/191 |
| 6,496,737 B2 | 12/2002 | Rudie et al. | 607/101 |
| 6,506,399 B2 | 1/2003 | Donovan | |
| 6,510,969 B2 | 1/2003 | Di Giovanni et al. | 222/402.2 |
| 6,514,290 B1 | 2/2003 | Loomas | 623/23.65 |
| 6,524,555 B1 | 2/2003 | Ashurst et al. | 424/45 |
| 6,526,976 B1 | 3/2003 | Baran | |
| 6,536,427 B2 | 3/2003 | Davies et al. | 128/203.15 |
| 6,546,928 B1 | 4/2003 | Ashurst et al. | 128/200.23 |
| 6,546,932 B1 * | 4/2003 | Nahon et al. | 128/898 |
| 6,547,776 B1 | 4/2003 | Gaiser et al. | 604/506 |
| 6,549,808 B1 | 4/2003 | Gisel et al. | 607/53 |
| 6,551,310 B1 | 4/2003 | Ganz et al. | 606/41 |
| 6,562,034 B2 | 5/2003 | Edwards et al. | 606/41 |
| 6,587,719 B1 | 7/2003 | Barrett et al. | 607/2 |
| 6,599,311 B1 | 7/2003 | Biggs et al. | 606/232 |
| 6,601,581 B1 | 8/2003 | Babaev | |
| 6,610,713 B2 | 8/2003 | Tracey | 514/343 |
| 6,620,415 B2 | 9/2003 | Donovan | |
| 6,623,742 B2 | 9/2003 | Voet | |
| 6,626,855 B1 | 9/2003 | Weng et al. | |
| 6,629,951 B2 | 10/2003 | Laufer et al. | 604/96.01 |
| 6,632,440 B1 | 10/2003 | Quinn | |
| 6,633,779 B1 | 10/2003 | Schuler et al. | 607/42 |
| 6,634,363 B1 | 10/2003 | Danek et al. | 128/898 |
| 6,645,496 B2 | 11/2003 | Aoki et al. | |
| 6,649,161 B1 | 11/2003 | Donovan | |

| Patent No. | Date | Inventor | Class |
|---|---|---|---|
| 6,656,960 B2 | 12/2003 | Puskas | 514/345 |
| 6,675,047 B1 | 1/2004 | Konoplev et al. | 607/50 |
| 6,676,686 B2 | 1/2004 | Naganuma | 607/1 |
| 6,681,136 B2 | 1/2004 | Schuler et al. | 607/44 |
| 6,692,494 B1 | 2/2004 | Cooper et al. | 606/46 |
| 6,711,436 B1 | 3/2004 | Duhaylongsod | 607/9 |
| 6,712,074 B2 | 3/2004 | Edwards et al. | 128/898 |
| 6,712,812 B2 | 3/2004 | Roschak et al. | 606/41 |
| 6,719,694 B2 | 4/2004 | Weng et al. | |
| 6,740,321 B1 | 5/2004 | Donovan | |
| 6,743,197 B1 | 6/2004 | Edwards | 604/103.01 |
| 6,743,413 B1 | 6/2004 | Schultz et al. | 424/45 |
| 6,749,606 B2 | 6/2004 | Keast et al. | 606/41 |
| 6,752,765 B1 | 6/2004 | Strobel et al. | 600/536 |
| 6,755,849 B1 | 6/2004 | Gowda et al. | 607/89 |
| 6,767,544 B2 | 7/2004 | Brooks et al. | |
| 6,773,711 B2 | 8/2004 | Voet et al. | |
| 6,776,991 B2 | 8/2004 | Naumann | 424/239.1 |
| 6,777,423 B2 | 8/2004 | Banholzer et al. | 514/291 |
| 6,778,854 B2 | 8/2004 | Puskas | 607/2 |
| 6,819,956 B2 | 11/2004 | DiLorenzo | 607/45 |
| 6,827,931 B1 | 12/2004 | Donovan | |
| 6,838,429 B2 | 1/2005 | Paslin | 514/2 |
| 6,838,434 B2 | 1/2005 | Voet | |
| 6,838,471 B2 | 1/2005 | Tracey | 514/343 |
| 6,841,156 B2 | 1/2005 | Aoki et al. | |
| 6,843,998 B1 | 1/2005 | Steward et al. | |
| 6,847,849 B2 | 1/2005 | Mamo et al. | |
| 6,861,058 B2 | 3/2005 | Aoki et al. | |
| 6,871,092 B2 | 3/2005 | Piccone | 607/3 |
| 6,872,206 B2 | 3/2005 | Edwards et al. | 606/41 |
| 6,872,397 B2 | 3/2005 | Aoki et al. | |
| 6,885,888 B2 | 4/2005 | Rezai | 607/9 |
| 6,908,928 B2 | 6/2005 | Banholzer et al. | 514/291 |
| 6,913,616 B2 | 7/2005 | Hamilton et al. | 607/89 |
| 6,934,583 B2 | 8/2005 | Weinberg et al. | 607/9 |
| 6,937,896 B1 | 8/2005 | Kroll | 607/9 |
| 6,937,903 B2 | 8/2005 | Schuler et al. | 607/42 |
| 6,957,106 B2 | 10/2005 | Schuler et al. | 607/44 |
| 6,961,622 B2 | 11/2005 | Gilbert | 607/148 |
| 6,970,742 B2 | 11/2005 | Mann et al. | 607/23 |
| RE38,912 E | 12/2005 | Walz et al. | 424/46 |
| 6,974,224 B2 | 12/2005 | Thomas-Benedict | 362/103 |
| 6,974,578 B1 | 12/2005 | Aoki et al. | |
| 6,978,174 B2 | 12/2005 | Gelfand et al. | 607/3 |
| 6,997,189 B2 | 2/2006 | Biggs et al. | 128/898 |
| 7,022,088 B2 | 4/2006 | Keast et al. | 601/2 |
| 7,022,105 B1 | 4/2006 | Edwards | 604/103.01 |
| 7,027,869 B2 | 4/2006 | Danek et al. | 607/42 |
| 7,070,800 B2 | 7/2006 | Bechtold-Peters et al. | 424/434 |
| 7,101,387 B2 | 9/2006 | Garabedian et al. | 607/105 |
| 7,104,987 B2 | 9/2006 | Biggs et al. | 606/34 |
| 7,112,198 B2 | 9/2006 | Satake | 606/41 |
| 7,142,910 B2 | 11/2006 | Puskas | 607/2 |
| 7,162,303 B2 | 1/2007 | Levin et al. | 607/44 |
| 7,175,644 B2 | 2/2007 | Cooper et al. | 606/191 |
| 7,179,257 B2 | 2/2007 | West et al. | 606/41 |
| 7,198,635 B2 | 4/2007 | Danek et al. | 607/96 |
| 7,200,445 B1 | 4/2007 | Dalbec et al. | 607/101 |
| 7,238,357 B2 | 7/2007 | Barron | |
| 7,241,295 B2 | 7/2007 | Maguire | 606/41 |
| RE39,820 E | 9/2007 | Banholzer et al. | 514/291 |
| 7,264,002 B2 | 9/2007 | Danek et al. | 128/898 |
| 7,273,055 B2 | 9/2007 | Danek et al. | 128/898 |
| 7,292,890 B2 | 11/2007 | Whitehurst et al. | 607/45 |
| 7,309,707 B2 | 12/2007 | Bender et al. | 514/291 |
| 7,310,552 B2 | 12/2007 | Puskas | 607/2 |
| RE40,045 E | 2/2008 | Palmer | 424/43 |
| 7,393,330 B2 | 7/2008 | Keast et al. | 601/2 |
| 7,422,563 B2 | 9/2008 | Roschak et al. | 601/2 |
| 7,422,584 B2 | 9/2008 | Loomas et al. | 606/32 |
| 7,425,212 B1 | 9/2008 | Danek et al. | 606/47 |
| 7,430,449 B2 | 9/2008 | Aldrich et al. | 607/42 |
| 7,462,162 B2 | 12/2008 | Phan et al. | 604/8 |
| 7,494,661 B2 | 2/2009 | Sanders | 424/239.1 |
| 7,517,320 B2 | 4/2009 | Wibowo et al. | 600/529 |
| 7,542,802 B2 | 6/2009 | Danek et al. | 607/42 |
| 7,553,307 B2 | 6/2009 | Bleich et al. | 606/1 |
| 7,556,624 B2 | 7/2009 | Laufer et al. | 604/514 |
| 7,594,925 B2 | 9/2009 | Danek et al. | 607/96 |
| 7,608,275 B2 | 10/2009 | Deem et al. | |
| 7,641,633 B2 | 1/2010 | Laufer et al. | 604/114 |
| 7,648,500 B2 | 1/2010 | Edwards et al. | 606/41 |
| 7,684,865 B2 | 3/2010 | Aldrich et al. | 607/40 |
| 7,708,712 B2 | 5/2010 | Phan et al. | 604/8 |
| 7,708,768 B2 | 5/2010 | Danek et al. | 607/96 |
| 7,734,535 B1 | 6/2010 | Burns | 705/37 |
| 7,740,017 B2 | 6/2010 | Danek et al. | 128/898 |
| 7,740,631 B2 | 6/2010 | Bleich et al. | 606/79 |
| 7,783,358 B2 | 8/2010 | Aldrich et al. | 607/40 |
| 2001/0044596 A1 | 11/2001 | Jaafar | |
| 2002/0002387 A1 | 1/2002 | Naganuma | 607/1 |
| 2002/0010495 A1 | 1/2002 | Freed et al. | 607/42 |
| 2002/0016344 A1 | 2/2002 | Tracey | 514/343 |
| 2002/0042564 A1 | 4/2002 | Cooper et al. | 600/407 |
| 2002/0042565 A1 | 4/2002 | Cooper et al. | 600/407 |
| 2002/0049370 A1 | 4/2002 | Laufer et al. | 600/300 |
| 2002/0072738 A1 | 6/2002 | Edwards et al. | 606/41 |
| 2002/0082197 A1 | 6/2002 | Aoki et al. | |
| 2002/0087153 A1 | 7/2002 | Roschak et al. | 606/27 |
| 2002/0087208 A1 | 7/2002 | Koblish et al. | 607/113 |
| 2002/0091379 A1 | 7/2002 | Danek et al. | 606/32 |
| 2002/0107515 A1 | 8/2002 | Edwards et al. | 606/41 |
| 2002/0111386 A1 | 8/2002 | Sekins et al. | 514/759 |
| 2002/0111619 A1 | 8/2002 | Keast et al. | 606/41 |
| 2002/0111620 A1 | 8/2002 | Cooper et al. | |
| 2002/0116030 A1 | 8/2002 | Rezai | 607/9 |
| 2002/0143302 A1* | 10/2002 | Hinchliffe et al. | 604/272 |
| 2002/0143373 A1 | 10/2002 | Courtnage et al. | 607/91 |
| 2002/0151888 A1 | 10/2002 | Edwards et al. | 606/41 |
| 2002/0183682 A1 | 12/2002 | Darvish et al. | 604/20 |
| 2002/0198512 A1 | 12/2002 | Seward | |
| 2002/0198570 A1 | 12/2002 | Puskas | 607/40 |
| 2002/0198574 A1 | 12/2002 | Gumpert | 607/58 |
| 2003/0018344 A1* | 1/2003 | Kaji et al. | 606/130 |
| 2003/0023287 A1 | 1/2003 | Edwards et al. | 607/101 |
| 2003/0027752 A1 | 2/2003 | Steward et al. | 514/12 |
| 2003/0050591 A1 | 3/2003 | McHale | |
| 2003/0070676 A1 | 4/2003 | Cooper et al. | 128/200.24 |
| 2003/0074039 A1 | 4/2003 | Puskas | 607/118 |
| 2003/0093128 A1 | 5/2003 | Freed et al. | 607/42 |
| 2003/0130657 A1 | 7/2003 | Tom et al. | 606/47 |
| 2003/0144572 A1 | 7/2003 | Oschman et al. | 600/16 |
| 2003/0159700 A1 | 8/2003 | Laufer et al. | 128/898 |
| 2003/0181949 A1 | 9/2003 | Whale | 607/2 |
| 2003/0202990 A1 | 10/2003 | Donovan et al. | |
| 2003/0211121 A1 | 11/2003 | Donovan | |
| 2003/0216791 A1 | 11/2003 | Schuler et al. | 607/44 |
| 2003/0216792 A1 | 11/2003 | Levin et al. | 607/48 |
| 2003/0216891 A1 | 11/2003 | Wegener | 702/188 |
| 2003/0233099 A1 | 12/2003 | Danaek et al. | 606/96 |
| 2004/0009180 A1 | 1/2004 | Donovan | |
| 2004/0010289 A1 | 1/2004 | Biggs et al. | 607/2 |
| 2004/0010290 A1 | 1/2004 | Schroeppel et al. | |
| 2004/0028676 A1* | 2/2004 | Klein et al. | 424/125 |
| 2004/0029849 A1 | 2/2004 | Schatzberg et al. | 514/179 |
| 2004/0030368 A1 | 2/2004 | Kemeny et al. | 607/88 |
| 2004/0044390 A1 | 3/2004 | Szeles | 607/142 |
| 2004/0059383 A1 | 3/2004 | Puskas | 607/1 |
| 2004/0073201 A1 | 4/2004 | Cooper et al. | 606/14 |
| 2004/0073278 A1 | 4/2004 | Pachys | 607/88 |
| 2004/0086531 A1 | 5/2004 | Barron | |
| 2004/0088030 A1 | 5/2004 | Jung, Jr. | 607/109 |
| 2004/0088036 A1 | 5/2004 | Gilbert | 607/148 |
| 2004/0091880 A1 | 5/2004 | Wiebusch et al. | |
| 2004/0106954 A1 | 6/2004 | Whitehurst et al. | 607/3 |
| 2004/0116981 A1 | 6/2004 | Mazar | 607/60 |
| 2004/0122488 A1 | 6/2004 | Mazar et al. | 607/60 |
| 2004/0122489 A1 | 6/2004 | Mazar et al. | 607/60 |
| 2004/0127942 A1 | 7/2004 | Yomtov et al. | 607/3 |
| 2004/0127958 A1 | 7/2004 | Mazar et al. | 607/60 |
| 2004/0142005 A1 | 7/2004 | Brooks et al. | |
| 2004/0147969 A1 | 7/2004 | Mann et al. | 607/17 |
| 2004/0147988 A1 | 7/2004 | Stephens | 607/108 |
| 2004/0151741 A1 | 8/2004 | Borodic | |
| 2004/0162597 A1 | 8/2004 | Hamilton et al. | 607/89 |
| 2004/0167509 A1 | 8/2004 | Taimisto | 606/41 |
| 2004/0167580 A1 | 8/2004 | Mann et al. | 607/17 |

| Publication No. | Date | Inventor | Class |
|---|---|---|---|
| 2004/0172075 A1 | 9/2004 | Shafer et al. | 607/9 |
| 2004/0172080 A1 | 9/2004 | Stadler et al. | 607/17 |
| 2004/0172084 A1 | 9/2004 | Knudson et al. | 607/40 |
| 2004/0175399 A1 | 9/2004 | Schiffman | |
| 2004/0176803 A1 | 9/2004 | Whelan et al. | 607/2 |
| 2004/0176805 A1 | 9/2004 | Whelan et al. | 607/2 |
| 2004/0182399 A1 | 9/2004 | Danek et al. | 128/898 |
| 2004/0186435 A1* | 9/2004 | Seward | 604/164.12 |
| 2004/0204747 A1 | 10/2004 | Kemeny et al. | 607/94 |
| 2004/0213813 A1 | 10/2004 | Ackerman | |
| 2004/0213814 A1 | 10/2004 | Ackerman | |
| 2004/0215289 A1 | 10/2004 | Fukui | 607/48 |
| 2004/0220556 A1 | 11/2004 | Cooper et al. | 606/1 |
| 2004/0220621 A1 | 11/2004 | Zhou et al. | 607/2 |
| 2004/0226556 A1 | 11/2004 | Deem et al. | |
| 2004/0230251 A1 | 11/2004 | Schuler et al. | 607/42 |
| 2004/0230252 A1 | 11/2004 | Kullok et al. | 607/48 |
| 2004/0243182 A1 | 12/2004 | Cohen et al. | 607/2 |
| 2004/0248188 A1* | 12/2004 | Sanders | 435/7.1 |
| 2004/0249416 A1 | 12/2004 | Yun et al. | 607/2 |
| 2004/0253274 A1 | 12/2004 | Voet | |
| 2005/0004609 A1 | 1/2005 | Stahmann et al. | 607/17 |
| 2005/0004631 A1 | 1/2005 | Benedict | 607/88 |
| 2005/0010263 A1 | 1/2005 | Schauerte | 607/48 |
| 2005/0010270 A1 | 1/2005 | Laufer | 607/88 |
| 2005/0015117 A1 | 1/2005 | Gerber | 607/39 |
| 2005/0019346 A1 | 1/2005 | Boulis | |
| 2005/0021092 A1 | 1/2005 | Yun et al. | 607/3 |
| 2005/0049615 A1 | 3/2005 | Cooper et al. | 606/140 |
| 2005/0056292 A1 | 3/2005 | Cooper | 128/898 |
| 2005/0059153 A1 | 3/2005 | George et al. | 435/446 |
| 2005/0060041 A1 | 3/2005 | Phan et al. | 623/23.7 |
| 2005/0060042 A1 | 3/2005 | Phan et al. | 623/23.7 |
| 2005/0060044 A1 | 3/2005 | Roschak et al. | 623/23.65 |
| 2005/0065553 A1 | 3/2005 | Ben Ezra et al. | 607/2 |
| 2005/0065562 A1 | 3/2005 | Rezai | 607/9 |
| 2005/0065567 A1 | 3/2005 | Lee et al. | 607/17 |
| 2005/0065573 A1 | 3/2005 | Rezai | 607/42 |
| 2005/0065574 A1 | 3/2005 | Rezai | 607/45 |
| 2005/0065575 A1 | 3/2005 | Dobak | 607/45 |
| 2005/0074461 A1 | 4/2005 | Donovan | |
| 2005/0076909 A1 | 4/2005 | Stahmann et al. | 128/204.23 |
| 2005/0080461 A1 | 4/2005 | Stahmann et al. | 607/17 |
| 2005/0085801 A1 | 4/2005 | Cooper et al. | 606/14 |
| 2005/0090722 A1 | 4/2005 | Perez | 600/315 |
| 2005/0096529 A1 | 5/2005 | Cooper et al. | 600/407 |
| 2005/0107829 A1 | 5/2005 | Edwards et al. | 607/2 |
| 2005/0107853 A1 | 5/2005 | Krespi et al. | |
| 2005/0125044 A1 | 6/2005 | Tracey | 607/45 |
| 2005/0137518 A1 | 6/2005 | Biggs et al. | 604/8 |
| 2005/0137611 A1 | 6/2005 | Escudero et al. | 606/108 |
| 2005/0137715 A1 | 6/2005 | Phan et al. | 623/23.65 |
| 2005/0143788 A1 | 6/2005 | Yun et al. | 607/46 |
| 2005/0149146 A1 | 7/2005 | Boveja et al. | 607/58 |
| 2005/0152924 A1 | 7/2005 | Voet | |
| 2005/0153885 A1 | 7/2005 | Yun et al. | 514/12 |
| 2005/0159736 A9 | 7/2005 | Danek et al. | 606/32 |
| 2005/0165456 A1 | 7/2005 | Mann et al. | 607/30 |
| 2005/0177144 A1 | 8/2005 | Phan et al. | 606/14 |
| 2005/0177192 A1 | 8/2005 | Rezai et al. | 607/3 |
| 2005/0182288 A1 | 8/2005 | Zabara | 600/14 |
| 2005/0187579 A1 | 8/2005 | Danek et al. | 607/1 |
| 2005/0222628 A1 | 10/2005 | Krakousky | 607/3 |
| 2005/0222635 A1 | 10/2005 | Krakovsky | 607/39 |
| 2005/0222651 A1 | 10/2005 | Jung, Jr. | 607/104 |
| 2005/0228054 A1 | 10/2005 | Tatton | 514/656 |
| 2005/0228459 A1 | 10/2005 | Levin et al. | 607/40 |
| 2005/0228460 A1 | 10/2005 | Levin et al. | 607/40 |
| 2005/0234523 A1 | 10/2005 | Levin et al. | 607/42 |
| 2005/0238693 A1 | 10/2005 | Whyte | 424/439 |
| 2005/0240241 A1 | 10/2005 | Yun et al. | 607/42 |
| 2005/0245992 A1 | 11/2005 | Persen et al. | 607/60 |
| 2005/0251213 A1 | 11/2005 | Freeman | 607/5 |
| 2005/0256028 A1 | 11/2005 | Yun et al. | 514/2 |
| 2005/0261747 A1 | 11/2005 | Schuler et al. | 607/42 |
| 2005/0267536 A1 | 12/2005 | Freeman et al. | 607/5 |
| 2005/0277993 A1 | 12/2005 | Mower | 607/9 |
| 2005/0283197 A1 | 12/2005 | Daum et al. | 607/17 |
| 2006/0015151 A1 | 1/2006 | Aldrich | 607/40 |
| 2006/0058780 A1 | 3/2006 | Edwards et al. | 606/40 |
| 2006/0062808 A1 | 3/2006 | Laufer et al. | 424/239.1 |
| 2006/0100666 A1 | 5/2006 | Wilkinson et al. | 607/1 |
| 2006/0106361 A1 | 5/2006 | Muni et al. | |
| 2006/0111755 A1 | 5/2006 | Stone et al. | 607/42 |
| 2006/0116749 A1 | 6/2006 | Willink et al. | 623/1.11 |
| 2006/0135984 A1 | 6/2006 | Kramer et al. | 606/192 |
| 2006/0135998 A1 | 6/2006 | Libbus et al. | 607/2 |
| 2006/0137698 A1 | 6/2006 | Danek et al. | 128/898 |
| 2006/0142801 A1 | 6/2006 | Demarais et al. | 607/2 |
| 2006/0167498 A1 | 7/2006 | DiLorenzo | 607/2 |
| 2006/0178703 A1 | 8/2006 | Huston et al. | 607/2 |
| 2006/0206150 A1 | 9/2006 | Demarais et al. | 607/3 |
| 2006/0212076 A1 | 9/2006 | Demarais et al. | 607/2 |
| 2006/0212078 A1 | 9/2006 | Demarais et al. | 607/3 |
| 2006/0225742 A1 | 10/2006 | Deem et al. | |
| 2006/0235474 A1 | 10/2006 | Demarais | 607/2 |
| 2006/0247617 A1 | 11/2006 | Danek et al. | 606/41 |
| 2006/0247618 A1 | 11/2006 | Kaplan et al. | 606/41 |
| 2006/0247619 A1 | 11/2006 | Kaplan et al. | 606/41 |
| 2006/0247683 A1 | 11/2006 | Danek et al. | 607/2 |
| 2006/0247726 A1 | 11/2006 | Biggs et al. | 607/42 |
| 2006/0247727 A1 | 11/2006 | Biggs et al. | 607/42 |
| 2006/0247746 A1 | 11/2006 | Danek et al. | 607/115 |
| 2006/0254600 A1 | 11/2006 | Danek et al. | 128/898 |
| 2006/0259028 A1 | 11/2006 | Utley et al. | 606/41 |
| 2006/0259029 A1 | 11/2006 | Utley et al. | 606/41 |
| 2006/0259030 A1 | 11/2006 | Utley et al. | 606/41 |
| 2006/0265014 A1 | 11/2006 | Demarais et al. | 607/2 |
| 2006/0265015 A1 | 11/2006 | Demarais et al. | 607/2 |
| 2006/0271111 A1 | 11/2006 | Demarais et al. | 607/2 |
| 2006/0276807 A1 | 12/2006 | Keast et al. | 606/140 |
| 2006/0276852 A1 | 12/2006 | Demarais et al. | 607/44 |
| 2006/0278243 A1 | 12/2006 | Danek et al. | 128/898 |
| 2006/0278244 A1 | 12/2006 | Danek et al. | 128/898 |
| 2006/0280772 A1 | 12/2006 | Roschak et al. | 424/426 |
| 2006/0280773 A1 | 12/2006 | Roschak et al. | 424/426 |
| 2006/0287679 A1 | 12/2006 | Stone | 607/2 |
| 2007/0021803 A1 | 1/2007 | Deem et al. | |
| 2007/0027496 A1 | 2/2007 | Parnis et al. | 607/42 |
| 2007/0060954 A1 | 3/2007 | Cameron et al. | 607/2 |
| 2007/0060990 A1 | 3/2007 | Satake | 607/101 |
| 2007/0062545 A1 | 3/2007 | Danek et al. | 128/898 |
| 2007/0066957 A1 | 3/2007 | Demarais et al. | 604/500 |
| 2007/0074719 A1 | 4/2007 | Danek et al. | 128/200.24 |
| 2007/0083197 A1 | 4/2007 | Danek et al. | 606/47 |
| 2007/0093802 A1 | 4/2007 | Danek et al. | 606/41 |
| 2007/0093809 A1 | 4/2007 | Edwards et al. | 606/41 |
| 2007/0100390 A1 | 5/2007 | Danaek et al. | 607/42 |
| 2007/0102011 A1 | 5/2007 | Danek et al. | 128/898 |
| 2007/0106292 A1 | 5/2007 | Kaplan et al. | 606/41 |
| 2007/0106296 A1 | 5/2007 | Laufer et al. | 606/50 |
| 2007/0106337 A1 | 5/2007 | Errico et al. | 607/40 |
| 2007/0106338 A1 | 5/2007 | Errico | 607/42 |
| 2007/0106339 A1 | 5/2007 | Errico et al. | 607/42 |
| 2007/0106348 A1 | 5/2007 | Laufer | 607/88 |
| 2007/0112349 A1 | 5/2007 | Danek et al. | 606/45 |
| 2007/0118184 A1 | 5/2007 | Danek et al. | 607/42 |
| 2007/0118190 A1 | 5/2007 | Danek et al. | 607/96 |
| 2007/0123922 A1 | 5/2007 | Cooper et al. | 606/191 |
| 2007/0123958 A1 | 5/2007 | Laufer | 607/93 |
| 2007/0123972 A1 | 5/2007 | Danek et al. | 607/101 |
| 2007/0129720 A1 | 6/2007 | Demarais et al. | 606/41 |
| 2007/0129760 A1 | 6/2007 | Demarais et al. | 607/2 |
| 2007/0129761 A1 | 6/2007 | Demarais et al. | 607/3 |
| 2007/0135875 A1 | 6/2007 | Demarais et al. | 607/96 |
| 2007/0173899 A1 | 7/2007 | Levin et al. | 607/40 |
| 2007/0191902 A1 | 8/2007 | Errico et al. | 607/42 |
| 2007/0197896 A1 | 8/2007 | Moll et al. | 600/407 |
| 2007/0203549 A1 | 8/2007 | Demarais et al. | 607/72 |
| 2007/0225768 A1 | 9/2007 | Dobak, III | 607/2 |
| 2007/0255028 A1 | 11/2007 | Roschak et al. | 606/185 |
| 2007/0265639 A1 | 11/2007 | Danek et al. | 606/130 |
| 2007/0265687 A1 | 11/2007 | Deem et al. | 607/72 |
| 2007/0267011 A1 | 11/2007 | Deem et al. | |
| 2008/0021369 A1 | 1/2008 | Deem et al. | |
| 2008/0051839 A1 | 2/2008 | Libbus et al. | 607/2 |
| 2008/0086107 A1 | 4/2008 | Roschak | 604/506 |
| 2008/0097424 A1 | 4/2008 | Wizeman et al. | 606/41 |

| | | | |
|---|---|---|---|
| 2008/0183248 A1 | 7/2008 | Rezai et al. .................. 607/62 |
| 2008/0194956 A1 | 8/2008 | Aldrich et al. ................ 600/439 |
| 2008/0213331 A1 | 9/2008 | Gelfand et al. ............... 424/422 |
| 2008/0243112 A1 | 10/2008 | De Neve .......................... 606/28 |
| 2008/0255642 A1 | 10/2008 | Zarins et al. .................... 607/99 |
| 2008/0262489 A1 | 10/2008 | Steinke ............................ 606/33 |
| 2008/0302359 A1 | 12/2008 | Loomas et al. ........... 128/200.24 |
| 2008/0306570 A1 | 12/2008 | Rezai et al. .................... 607/42 |
| 2008/0312543 A1 | 12/2008 | Laufer et al. .................. 600/486 |
| 2009/0018473 A1 | 1/2009 | Aldrich et al. .................... 601/2 |
| 2009/0018538 A1 | 1/2009 | Webster et al. ................. 606/41 |
| 2009/0030477 A1 | 1/2009 | Jarrard ............................ 607/42 |
| 2009/0036948 A1 | 2/2009 | Levin et al. ..................... 607/44 |
| 2009/0043301 A1 | 2/2009 | Jarrard et al. ................... 606/41 |
| 2009/0043302 A1 | 2/2009 | Ford et al. ...................... 606/41 |
| 2009/0062873 A1 | 3/2009 | Wu et al. .......................... 607/2 |
| 2009/0069797 A1 | 3/2009 | Danek et al. .................... 606/33 |
| 2009/0076409 A1 | 3/2009 | Wu et al. ........................ 600/547 |
| 2009/0076491 A1 | 3/2009 | Roschak et al. ................ 606/21 |
| 2009/0112203 A1 | 4/2009 | Danek et al. .................... 606/33 |
| 2009/0124883 A1 | 5/2009 | Wibowo et al. ................ 600/407 |
| 2009/0131765 A1 | 5/2009 | Roschak et al. ............... 600/301 |
| 2009/0131928 A1 | 5/2009 | Edwards et al. ............... 606/33 |
| 2009/0143678 A1 | 6/2009 | Keast et al. .................... 600/439 |
| 2009/0143705 A1 | 6/2009 | Danek et al. ...................... 601/3 |
| 2009/0143776 A1 | 6/2009 | Danek et al. .................... 606/21 |
| 2009/0155336 A1 | 6/2009 | Rezai ............................ 424/423 |
| 2009/0192508 A1 | 7/2009 | Laufer et al. .................... 606/41 |
| 2009/0204005 A1 | 8/2009 | Keast et al. .................... 600/461 |
| 2009/0204119 A1 | 8/2009 | Bleich et al. .................... 606/79 |
| 2009/0248011 A1 | 10/2009 | Hlavka et al. .................. 606/41 |
| 2009/0275840 A1 | 11/2009 | Roschak et al. ............... 600/467 |
| 2009/0275878 A1 | 11/2009 | Cambier et al. ................ 604/21 |
| 2009/0287087 A1 | 11/2009 | Gwerder et al. ............... 600/463 |
| 2009/0306644 A1 | 12/2009 | Mayse et al. .................... 606/33 |
| 2009/0318904 A9 | 12/2009 | Cooper et al. ..................... 606/1 |
| 2010/0003282 A1 | 1/2010 | Deem et al. |
| 2010/0070004 A1 | 3/2010 | Hlavka et al. .................. 607/62 |
| 2010/0076518 A1 | 3/2010 | Hlavka et al. .................. 607/62 |
| 2010/0094231 A1 | 4/2010 | Bleich et al. .................. 604/274 |
| 2010/0116279 A9 | 5/2010 | Cooper ......................... 128/898 |
| 2010/0137860 A1 | 6/2010 | Demarais et al. ............... 606/41 |
| 2010/0160906 A1 | 6/2010 | Jarrard ............................ 606/33 |
| 2011/0015548 A1 | 1/2011 | Aldrich et al. .................... 601/2 |
| 2011/0046432 A1 | 2/2011 | Simon et al. .................... 600/14 |
| 2011/0060380 A1 | 3/2011 | Gelfand et al. ................. 607/42 |
| 2011/0079230 A1 | 4/2011 | Danek et al. .................. 128/898 |
| 2011/0093032 A1 | 4/2011 | Boggs, II et al. .............. 607/42 |
| 2011/0112400 A1 | 5/2011 | Emery et al. .................. 600/14 |
| 2011/0118725 A1 | 5/2011 | Mayse et al. .................... 606/33 |
| 2011/0152855 A1 | 6/2011 | Mayse et al. .................... 606/33 |

FOREIGN PATENT DOCUMENTS

| | | |
|---|---|---|
| EP | 0 643 982 | 3/1995 |
| EP | 1 143 864 | 10/2001 |
| EP | 1 271 384 | 1/2003 |
| EP | 1 281 366 | 2/2003 |
| EP | 1 326 549 | 7/2003 |
| EP | 1326548 | 7/2003 |
| EP | 1 400 204 | 3/2004 |
| EP | 1 588 662 | 10/2005 |
| RU | 2053814 | 2/1996 |
| WO | 89/11311 | 11/1989 |
| WO | 93/01862 | 2/1993 |
| WO | 93/16632 | 9/1993 |
| WO | 94/07446 | 4/1994 |
| WO | 95/01075 | 1/1995 |
| WO | 97/25917 | 7/1997 |
| WO | 98/18391 | 5/1998 |
| WO | 99/42047 | 8/1999 |
| WO | WO 00/10598 A2 | 3/2000 |
| WO | 00/62699 | 10/2000 |
| WO | 00/66017 | 11/2000 |
| WO | 01/00114 | 1/2001 |
| WO | 01/70114 | 9/2001 |
| WO | 01/89526 | 11/2001 |
| WO | 03/073358 | 9/2003 |
| WO | 03/088820 | 10/2003 |
| WO | 2004/078252 | 9/2004 |
| WO | 2004/082736 | 9/2004 |
| WO | WO 2004/101028 A2 | 11/2004 |
| WO | 2005/006963 | 1/2005 |
| WO | 2005/006964 | 1/2005 |
| WO | 2006/053308 | 5/2006 |
| WO | 2006/053309 | 5/2006 |
| WO | 2006/116198 | 11/2006 |
| WO | 2007/061982 | 5/2007 |
| WO | 2007/143665 | 12/2007 |
| WO | 2008/005953 | 1/2008 |
| WO | 2008/024220 | 2/2008 |
| WO | 2008/051706 | 5/2008 |
| WO | 2008/063935 | 5/2008 |
| WO | 2009/009236 | 1/2009 |
| WO | 2009/015278 | 1/2009 |

OTHER PUBLICATIONS

Korpela et al., "Comparison of Tissue Reactions in the Tracheal Mucosa Surrounding a Bioabsorbable and Silicone Airway Stents", Annals of Thoracic Surgery,199B, pp. 1772-1776, Elsevier Science Inc.

Tsuji et al. "Biodegradable Stents as a Platform to Drug Loading" Journal of Cardiovascular Interventions, 2003, pp. 13-16, vol. 5, Taylor and Francis.

Ahnert-Hilger et al., "Introduction of Macromolecules into Bovine Adrenal-Medullary Chromaffin Cells and Rat Pheochromacytoma Cells (PC12) by Permeabilization with Streptolysin-Oinhibitory Effect of Tetanus Toxin on Catecholamine Secretion," J. Neurochem. Jun. 1989; 52(6):1751-1758.

Bigalke et al., "Clostridial Toxins", Handbook of Experimental Pharmacology (Aktories, K., and Just, I., eds) 2000, 145:407-443, Springer Verlag, Berlin, Heidelberg.

Bittner et al., "Isolated Light Chains of Botulinum Neurotoxins Inhibit Exocytosis. Studies in Digitonin-Permeabilized Chromaffin Cells." J Biol Chem Jun. 25, 1989; 264(18):10354-10360.

Buzzi, "Diphteria Toxin Treatment of Human Advanced Cancer," Cancer Research, 1982, 42:2054-2058.

Chaddock et al "Expression and Purification of Catalytically Active, Non-Toxic Endopeptidase Derivatives of *Clostridium botulinum* Toxin Type A," Protein Expression and Purification, Jul. 2002, 25( 2): 219-228.

Chang, "Cell Poration and Cell Fusion Using an Oscillating Electric Field," Biophys J. Oct. 1989; 56(4): 641-652.

De Paiva et al., "Light chain of *botulinum* neurotoxin is active in mammalian motor nerve terminals when delivered via liposomes," FEBS Lett. Dec. 17, 1990;277(1-2):171-174.

Guzman et al., "Bioeffects Caused by Changes in Acuostic Cavitation Bubble Density and Cell Concentration: A Unified Explanation Based on Cell-to-Bubble Ratio and Blast Radius," Ultrasound in Med. & Biol., 2003, 29(8): 1211-1222.

Kistner et al, "Reductive Cleavage of Tetanus Toxin and *Botulinum* Neurotoxin A by the Thioredoxin System from Brain. Evidence for Two Redox Isomers of Tetanus Toxin," Naunyn Schmiedebergs Arch Pharmacol. Feb. 1992; 345(2):227-34.

Kreitman, "Taming Ricin," Nature Biotechnology, 2003, 21:372-374.

RAJ, Editorial, Pain Practice, 2004; 4(1S): S1-S3.

Shaari et al., "Rhinorrhea is Decreased in Dogs After Nasal Application of Botulinum Toxin," Otolaryngol Head Neck Surg 1995;112:566-571.

Simpson et al., "Isolation and Characterization of the Botulinum Neurotoxins," Methods Enzymol. 1988; 165:76-85.

Sundaram et al., "An Experimental and Theoretical Analysis of Ultrasound-Induced Permeabilization of Cell Membranes," Biophysical Journal, May 1, 2003; 84( 5): 3087-3101.

Unal et al, "Effect of Botulinum Toxin Type A on Nasal Symptoms in Patients with Allergic Rhinitis: A Double-blind, Placebo-controlled Clinical Trial," Acta Oto-Laryngologica,, Dec. 2003, 123(9):1060-0163.

Weaver, "Electroporation: A General Phenomenon for Manipulating Cells and Tissues," Cell Biochem. Apr. 1993; 51(4):426-35.

Abbott, "Present Concepts Relative to Autonomic Nerve Surgery in the Treatment of Pulmonary Disease," *American Journal of Surgery* 90:479-489, 1955.

Babichev et al., "Clinico-morphological comparisons in patients with bronchial asthma after denervation of the lungs," *Sov Med.* 12:13-16, 1985.

Babichev et al., "Long-term results of surgical treatment of bronchial asthma based on adaptive response," *Khirurgiia (Mosk)* 4:5-11, 1993.

Babichev et al., "Partial deneration of the lungs in bronchial asthma," *Khirurgiia (Mosk)* 4:31-35, 1985.

Barlaw, "Surgical Treatment of Asthma," *Postgrad Med. Journal* 25:193-196, 1949.

Bester et al., "Recovery of C-Fiber-Induced Extravasation Following Peripheral Nerve Injury in the Rat," *Experimental Neurology* 154:628-636, 1998.

Bittner et al., "Isolated Light Chains of Botulinum Neurotoxins Inhibit Exocytosis," *The Journal of Biological Chemistry* 264(18):10354-10360, 1989.

Brody et al., "Mucociliary clearance after lung denervation and bronchial transection," *J. Applied Physiology* 32(2):160-164, 1972.

Canning et al., "Reflex Mechanisms in Gastroesophageal Reflux Disease and Asthma," *The American Journal of Medicine* 115(3A):45S-48S, 2003.

Canning et al., "Reflex Mechanisms in Gastroesophageal Reflux Disease and Asthma," *Am J Med.* 115(Suppl 3A):45S-48S, 2003. (Abstract only.).

Canning, "Reflex regulation of airway smooth muscle tone," *J Appl. Physiol.* (101):971-985, 2006.

Chernyshova et al., "The Effect of Low-Energy Laser Radiation in the Infrared Spectrum on Bronchial Patency in Children with Bronchial Asthma," *Vopr Kurortol Fizioter Lech Fiz Kult* 2:11-14, 1995. (+ English translation, 6 pages.).

Chumakov et al., "Morphologic Studies of Bronchial Biopsies in Chronic Bronchitis Before and After Treatment," *Arkh. Patol.* 57(6):21-25, 1995. (+ English abstract and translation, 8 pages.).

Crimi et al., "Protective effects of inhaled ipratropium bromide on bronchoconstriction induced by adenosine and methacholine in asthma," *Eur Respir J* 5:560-565, 1992.

Feshenko et al., "Clinico-morphological comparisons in the laser therapy of chronic bronchitis patients," *Lik Sprava.* (10-12):75-79, 1993. (+ English abstract, 1 Page.).

Gelb et al., "Laser in treatment of lung cancer," *Chest* 86(5):662-666, 1984.

Gerasin et al., "Endobronchial electrosurgery," *Chest* 93:270-274, 1988.

Gibson et al., "Gastroesophageal Reflux Treatment for Asthma in Adults and Children," *Cochrane Database Syst. Rev.* 2:CD001496, 2003. (Abstract only.).

Glanville et al., "Bronchial responsiveness after human heart-lung transplantation," *Chest* 97(6):1360-1366, 1990.

Glanville et al., "Bronchial responsiveness to exercise after human cardiopulmonary transplantation," *Chest* 96(2):81-286, 1989.

Gosens et al., "Muscarinic receptor signaling in the pathophysiology of asthma and COPD," *Respiratory Research* 7(73):1-15, 2006.

Groeben et al. "High Thoracic Epidural Anesthesia Does Not Alter Airway Resistance and Attenuates the Response to an Inhalational Provocation Test in Patients with Bronchial Hyperreactivity," *Anesthesiology* 81(4):868-874, 1994.

Guarini et al., "Efferent Vagal Fibre Stimulation Blunts Nuclear Factor-kB Activation and Protects Against Hypovolemic Hemmorrhagic Shock," *Circulation* 107:1189-1194, 2003.

Hainsworth et al., "Afferent lung denervation by brief inhalation of steam," *Journal of Applied Physiology* (34)5: 708-714, 1972.

Harding, "Recent Clinical Investigations Examining the Association of Asthma and Gastroesophageal Reflux," *Am J Med.* 115(Suppl 3A):39S-44S, 2003. (Abstract only.).

Hiraga, "Experimental surgical therapy of bronchial asthma. The effect of denervation in dogs," *Nihon Kyobu Shikkan Gakkai Zasshi* 19(1):46-56, 1981.

Hoffmann et al., "Inhibition of Histamine-Induced Bronchoconstriction in Guinea Pig and Swine by Pulsed Electrical Vagus Nerve Stimulation," *Neuromodulation: Technology at the Neural Interface*:1-9, 2009.

Hooper et al., "Endobronchial electrocautery," *Chest* 87(6):12-714, 1985.

Ivanyuta OM, et al., "Effect of Low-Power Laser Irradiation of *Bronchia mucosa* on the State of Systemic and Local Immunity in Patients with Chronic Bronchitis," *Problemy Tuberkuleza* 6:26-29, 1991.

Jammes et al., "Assessment of the Pulmonary Origin of Bronchoconstrictor Vagal Tone," *J. Physiol.* 291: 305-316, 1979.

Jiang et al., "Effects of Antireflux Treatment on Bronchial Hyperresponsiveness and Lung Function in Asthmatic Patients with Gastroesophageal Reflux Disease," *World J Gastroenterol.* 9:1123-1125, 2003. (Abstract only.).

Karashurov et al., "Electrostimulation in the therapy of bronchial asthma," *Klin Med (Mosk)* 79(11):38-41, 2001.

Karashurov et al., "Radiofrequency electrostimulation of carotid sinus nerves for the treatment of bronchial asthma," *Khirurgiia (Mosk)* 12:2-6, 1999.

Khmel'kova et al., "Does laser irridation affect bronchial obstruction?," *Probl Tuberk* 3:41-42, 1995. (Abstract only.).

Khoshoo et al., "Role of Gastroesophageal Reflux in Older Children with Persistent Asthma," *Chest* 123:1008-1013, 2003. (Abstract only.).

Kiljander, "The Role of Proton Pump Inhibitors in the Management of Gastroesophageal Reflux Disease-Related Asthma and Chronic Cough," *Am J Med.* 115(Suppl 3A):65S-71S, 2003. (Abstract only.).

Kletskin et al., "Value of assessing the autonomic nervous system in bronchial asthma in selecting the surgical treatment method," *Khirurgiia (Mosk)* 7:91-95, 1987.

Kliachkin et al., "Bronchoscopy in the treatment of bronchial asthma of infectious allergic origin," *Ter Arkh* 54(4):76-79, 1982.

Kuntz, "The Autonomic Nervous System in Relation to the Thoracic Viscera," *Chest* 10:1-18, 1944.

Lennerz et al., "Electrophysiological characterization of vagal afferents relevant to mucosal nociception in the rat upper oesophagus," *J. Physiol.* 582(1):229-242, 2007.

Levin, "The Treatment of Bronchial Asthma by Dorsal Sympathectomy," *Annals of Surgery* 102(2):161-170, 1935.

Liou et al., "Causative and Contributive Factors to Asthmas Severity and Patterns of Medication Use in Patients Seeking Specialized Asthma Care," *Chest* 124:1781-1788, 2003. (Abstract only.).

Magnussen et al., "Effect of Inhaled Ipratropium Bromide on the Airway Response to Methacholine, Histamine, and Exercise in Patients with Mild Bronchial Asthma," *Respiration* 59:42-47, 1992.

Mathew et al., "Gastro-oesophageal reflux and bronchial asthma: current status and future directions," *Postgrad Med. J.* 80:701-705, 2004.

McKay et al., "Autocrine regulation of asthmatic airway inflammation: role of airway smooth muscle," *Respir Res* 3(11):1-13, 2002.

Mehta et al., "Effect of endobronchial radiation therapy on malignant bronchial obstruction," *Chest* 97(3):662-665, 1990.

Meshalkin et al., "Partial denervation of the pulmonary hilus as one of the methods of surgical treatment of bronchial asthma," *Grudn Khir* 1:109-111, 1975.

Moore, Keith L., *Clinically Oriented Anatomy*, 2$^{nd}$ ed., Williams & Wilkins, Baltimore, 1985, pp. 85 and 87. (Abstract only.).

Netter, Frank H., *The Ciba Collection of Medical Illustrations*: vol. 7, Respiratory System, CIBA-GEIGY Corporation, West Caldwell, 1979, p. 23, section 1. (Abstract only.).

Ochs, Matthias et al., Fisherman, Alfred P., et al. (eds), *Functional Design of the Human Lung for Gas Exchange*, 4$^{th}$ ed., McGraw Hill Medical, New York, 2008, Chap. 2, "Fisherman's Pulmonary Diseases and Disorders." (Abstract only.).

Ovcharenko et al., "Endobronchial use of low-frequency ultrasound and ultraviolet laser radiation in the complex treatment of patients with suppurative bronchial diseases," *Probl Tuberk* 3:40-42, 1997. (Abstract only.).

Overholt, "Glomectomy for Asthma," *Dis Chest* 40:605-610, 1961.

Petrou, et al., "Bronchoscopic Diathermy Resection and Stent Insertion: a Cost Effective Treatment for Tracheobronchial Obstruction," *Thorax* 48:1156-1159, 1993.

Polosukhin, "Dynamics of the ultrastructural changes in blood and lymphatic capillaries of bronchi in inflammation and following endobronchial laser therapy," *Virchows Arch.* 431:283-290, 1997.

Polosukhin, "Regeneration of Bronchial Epithelium on Chronic Inflammatory Changes Under Laser Treatment," *Path. Res. Pract.* *192*:909-918, 1996.

Polosukhin, "Ultrastructural study of the destructive and repair processes in pulmonary inflammation and following endobronchial laser therapy," *Virchows Arch. 435*:13-19, 1999.

Polosukhin, "Ultrastructure of the Blood and Lymphatic Capillaries of the Respiratory Tissue During Inflammation and Endobronchial Laser Therapy," *Ultrastructural Pathology 24*:183-189, 2000.

Provotorov VM, et al., "Clinical Efficacy of Treatment of Patients with Non-Specific Pulmonary Diseases by Using Low-Power Laser Irradiation and Performing Intrapulmonary Drug Administration," *Terapevichesky Arkhiv 62*:18-23, 1991.

Ramirez et al., "Sympathetomy in Bronchial Asthma," *J. A. M. A. 84* (26):2002-2003, 1925.

Rienhoff et al., "Treatment of Intractable Bronchial Asthma by Bilateral Resection of the Posterior Pulmonary Plexus," *Arch Surg 37*(3):456-469, 1938.

Savchenko et al., "Adaptation of regulatory physiological systems in surgical treatment of patients with bronchial asthma," *Klin Med (Mosk) 74*(7):38-39, 1996.

Sengupta, "Part 1 Oral cavity, pharynx and esophagus—Esophageal sensory physiology," *GI Motility online*:17 pages, 2006.

Sepulveda et al., "Treatment of Asthmatic Bronchoconstriction by Percutaneous Low Voltage Vagal Nerve Stimulation: Case Report," *Internet Journal of Asthma, Allergy, and Immunology 7*(2):3 pages, 2009.

Sheski FD, et al., "Cryotherapy, Electrocautery, and Brachytherapy," *Clinics in Chest Medicine 20*(1):123-138, Mar. 1999.

Sil'vestrov et al., "The Clinico-Pathogenetic Validation and Efficacy of the Use of Low-Energy Laser Irradiation and Glucocorticoids in the Treatment of Bronchial Asthma Patients," *Ter Arkh 63*(11), 87-92, 1991.

Simonsson et al., "Role of Autonomic Nervous System and the Cough Reflex in the Increased Responsiveness of Airways in Patients with Obstructive Airway Disease," *The Journal of Clinical Investigation 46*(11): 1812-1818, 1967.

Sontag et al., "Asthmatics with Gastroesophageal Reflux: Long-term Results of a Randomized Trial of Medical and Surgical Antireflux Therapies," *Am J Gastroenterol. 98*:987-999, 2003. (Abstract only.).

Stein, "Possible Mechanisms of Influence of Esophageal Acid on Airway Hyperresponsiveness," *Am J Med. 115*(Suppl 3A):55S-59S, 2003. (Abstract only.).

Takino et al., "Surgical Removal of the Carotid Body and its Relation to the Carotid Chemoreceptor and Baroreceptor Reflex in Asthmatics," *Dis Chest 47*:129-138, 1965.

Tsugeno et al., "A Proton-Pump Inhibitor, Rabeprazole, Improves Ventilatory Function in Patients with Asthma Associated with Gastroesophageal Reflux," *Scand J Gastroenterol. 38*:456-461, 2003. (Abstract only.).

Van Boxem TJM, et al., "Tissue Effects of Bronchoscopic Electrocautery," *Chest 117*(3):887-891, Mar. 1999.

van der Velden et al., "Autonomic Innervation of Human Airways: Structure, Function, and Pathophysiology in Asthma," *Neuroimmunomodulation 6*:145-159, 1999.

Verhein et al., "Neural Control of Airway Inflammation," *Current Allergy and Asthma Reports 9*:484-490, 2009.

Vorotnev et al., "Treatment of Patients with Chronic Obstructive Bronchitis Using Low Energy Laser at a General Rehabilitation Center," *Therapeutic Archive 3*:17-19, 1997. (+English translation, 4 pages).

Wahidi et al., "State of the Art: Interventional Pulmonology," *Chest 131*:261-274, 2007.

Wirtz et al., "Bilateral Lung Transplantation for Severe Persistent and Difficult Asthma," *The Journal of Heart and Lung Transplantation 24*(10):1700-1703, 2005.

Laufer, "Method and Apparatus for Treating Smooth Muscles in the Walls of Body Conduits," U.S. Appl. No. 09/095,323, filed Jun. 10, 1998, 25 pages.

\* cited by examiner

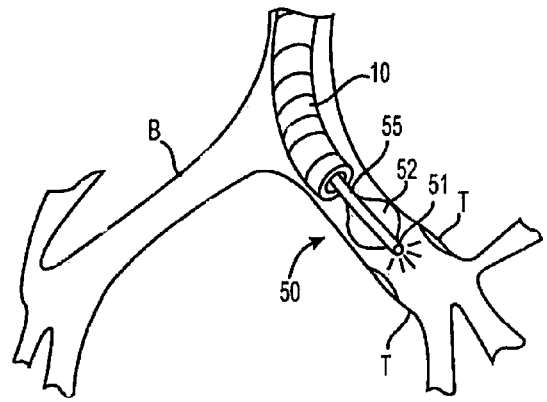
FIG. 8
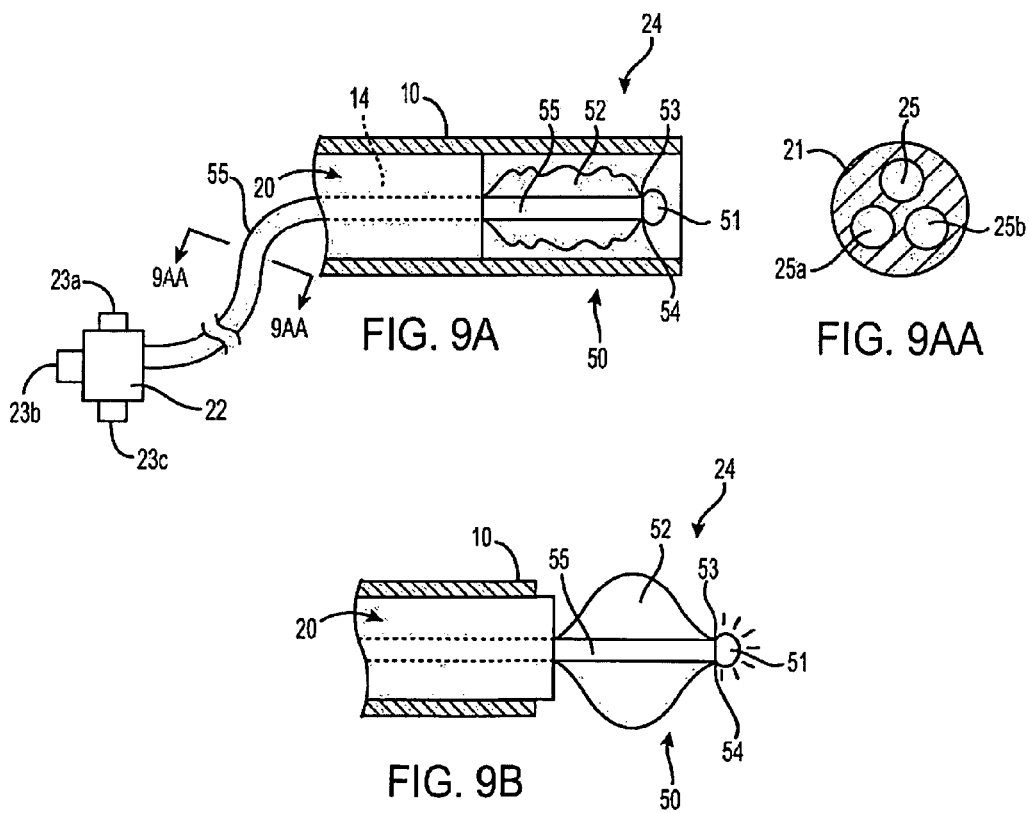
FIG. 9A
FIG. 9AA
FIG. 9B

APPARATUS FOR TREATING ASTHMA USING NEUROTOXIN

CROSS-REFERENCES TO RELATED APPLICATIONS

The present application is a continuation of U.S. patent application Ser. No. 10/437,882, filed May 13, 2003, the full disclosure of which is incorporated herein by reference.

BACKGROUND OF THE INVENTION

Field of the Invention

The present invention relates to apparatus for treating asthma by controlled delivery of neurotoxin 5 using a neurotoxin applicator assembly.

The lung is made up of progressively smaller bronchial bifurcations stemming downward from the trachea. The trachea and proximal bronchi are lumens consisting of an outer layer of fascia surrounding a U-shaped inner cartilaginous layer, wherein the open portion of the U is spanned by smooth muscle. Inside the cartilaginous layer are a collagenous elastic layer and an innermost epithelial layer. Mucus secreting goblet cells and transport cilial cells are interspersed within these inner layers.

As the bronchi branch and get smaller, the cartilaginous layer changes from a U-shape to irregular and helical shapes. In addition, the smooth muscle layer becomes helical bands surrounding the entire circumference of the bronchi, the goblet cells gradually decrease in numbers and the ciliated cells get smaller and fewer in number. In the most distal bronchi, the outer cartilaginous layer disappears completely, the smooth muscle layer becomes the outermost layer and goblet cells and ciliated cells disappear completely.

Asthma is a complex disease of the bronchial tree, characterized by airway hyperresponsiveness to allergens, stress and environmental triggers. Environmental triggers include irritants such as pollutants and non-allergenic triggers such as exposure to cold air. Airway hyperresponsiveness results in acute narrowing of the entire bronchial tree reducing airflow through the lungs, compromising respiration and limiting gas exchange in the alveoli. The narrowing of the bronchial tree is a result of three basic characteristic physiologic responses: (1) smooth muscle contraction; (2) increased mucus production; and (3) edema caused by arterial dilatation and increased arterial permeability. The triggering mechanisms for these physiologic responses are part of the body's inflammatory response system.

Chronic uncontrolled asthma can result in structural changes to the bronchial wall itself. Smooth muscle hyperplasia results in thickening of the smooth muscle components of the bronchial wall. Thickening of the subepithelial collagen layer that lies between the airway epithelium and the smooth muscle layer results in progressive stiffening of the wall of the bronchi. Studies have shown that stiffening of the airway wall results in more profound narrowing of the airway for a given asthma attack. This is due to changes in the ability of the mucosal layer to fold in response to the smooth muscle layer contraction.

Recently, the controlled injection of neurotoxin has become a common procedure for controlling skeletal muscle spasms. A frequently used neurotoxin for this procedure is the botulinum toxin, serotype A, sold commercially by Allergan, Inc. as BOTOX®. BOTOX® neurotoxin blocks the release of neurotransmitter from the nerves that control the contraction of the target muscles. Many applications for BOTOX® neurotoxin have been proposed and/or clinically tested, including cervical dystonia, cosmetic relief of frown lines and tremor associated with cerebral palsy. Recently, BOTOX® neurotoxin has become the subject of clinical study for the relief of hyperhidrosis (profuse sweating) and hypersalivation. These studies indicate that BOTOX® neurotoxin can be used to control the action of cholinergic parasympathetic nerves as well as large skeletal muscle groups. The recent findings open the possibility of using neurotoxins such as BOTOX® neurotoxin to control some of the main mechanisms of airway narrowing in asthmatic attacks, specifically smooth muscle contraction and hypersecretion of mucus from the goblet cells. Additionally, there is evidence that some part of the inflammatory response of asthma is stimulated by the release of the neurotransmitters which BOTOX® neurotoxin inhibits. This opens the possibility that BOTOX® neurotoxin may also work to mitigate the inflammatory cycle itself.

The use of neurotoxin for the control of asthma is described in U.S. Pat. No. 6,063,768 to First, wherein asthma is included in a list of neurogenic inflammatory disorders that may be controlled through the action of neurotoxins such as BOTOX® neurotoxin. That patent also describes that BOTOX® neurotoxin could be aerosolized and introduced into the lungs. An earlier patent, U.S. Pat. No. 5,766,605 to Sanders, et al. describes the use of BOTOX® neurotoxin to treat asthma and COPD, but does not describe the methods or devices used to do so. Further mention of BOTOX® neurotoxin in connection with asthma is provided in a press release dated Feb. 7, 2003 by the University of Alberta in describing the work of Dr. Redwan Moqbel. The release mentions that Dr. Moqbel and others are researching the possible use of neurotoxins such as tetanus and botulinum toxin to prevent eosinophils from activating and starting the inflammatory cascade that results in an asthma attack.

While it may be possible to simply aerosolize neurotoxins for introduction into the lungs, introducing it into the patient through traditional inhalation means would expose the mouth, tongue, epiglottis, vocal cords, etc. to the actions of the neurotoxin, with obvious deleterious results. Much more controlled and direct application of the neurotoxin to the desired tissue is required for safe and effective therapy.

Accordingly, it would be desirable to provide apparatus that enables controlled delivery of a neurotoxin to target treatment areas within a patient's bronchial airways.

It also would be desirable to provide an apparatus permitting the controlled injection of neurotoxin into the bronchial wall of a patient.

It would further be desirable to provide a needle-less injection apparatus to eliminate potential complications related to the presence of needles within a patient's bronchial airways.

Additionally, it would be desirable to provide an apparatus permitting the application of neurotoxin onto a target treatment area within a patient's bronchial airways.

BRIEF SUMMARY OF THE INVENTION

In view of the foregoing, it is an object of the present invention to provide apparatus that enables the controlled delivery of a neurotoxin to target treatment areas within a patient's bronchial airways.

It is a further object of the present invention to provide an apparatus permitting the controlled injection of neurotoxin into the bronchial wall of a-patient.

It is an additional object of the present invention to provide a needle-less injection apparatus to eliminate potential complications related to the presence of needles within a patient's bronchial airways.

It is another object of the present invention to provide an apparatus permitting the application of neurotoxin onto a target treatment area within a patient's bronchial airways.

These and other objects of the present invention are accomplished by providing an intrabronchial neurotoxin delivery system for controlled delivery of neurotoxin to a target treatment area within a patient's bronchial airways to lessen the effects of asthma. The introduction of neurotoxin into the bronchial airways disables the hyperresponsive smooth muscle layer and controls the hypersecretion of mucus.

The intrabronchial neurotoxin delivery system preferably includes a bronchoscope and neurotoxin applicator assembly. The neurotoxin applicator assembly may be a needle assembly, rotating needle assembly, needle-less injection assembly or a nebulizer assembly.

In a first illustrative embodiment, the neurotoxin applicator assembly comprises a needle assembly including at least one needle having a lumen in fluid communication with a source of liquid neurotoxin. The needles are preformed to contract radially when disposed within a lumen, such as a lumen of the bronchoscope, but may be extended to penetrate and inject small doses of neurotoxin into the bronchial wall of a patient.

In an alternative embodiment, the neurotoxin applicator assembly comprises a rotating needle assembly including plural needles disposed along the circumference of a wheel. Again, the needles include lumens in fluid communication with a source of liquid neurotoxin. In operation, the wheel is adapted to be rolled across a target treatment area about a central hub. Optionally, the rotating needle assembly may include a fender to protect a portion of the bronchial wall substantially opposite the target treatment area.

In another alternative embodiment, the neurotoxin applicator assembly comprises a needle-less injection assembly including a shaft having at least one port in fluid communication with a source of liquid neurotoxin. The needle-less injection assembly can be used to inject neurotoxin into the bronchial wall without needle penetration. Optionally, an inflatable balloon may be provided to help position the at least one port adjacent the target treatment area.

In yet a further alternative embodiment, the neurotoxin applicator assembly comprises a nebulizer assembly including an atomizer in fluid communication with a source of liquid neurotoxin. The atomizer converts the liquid neurotoxin into a fine spray or mist that is directed onto the target treatment area. The particle size of the mix can be controlled using injection pressure or atomizer head design to access specific portions of the lung adjacent to or downstream of the treatment device. An inflatable balloon optionally may be provided to facilitate positioning the atomizer adjacent the target treatment area. The balloon also serves to isolate the lung segment downstream of the device to prevent reflux of the mist into undesired portions of the airway. In addition, lumens optionally may be disposed between the balloon and atomizer to provide a ventilation system that allows pressure control of the treatment area to prevent over-inflation of the lung, mixing of the atomized fluid, and evacuation of remaining mist at termination of therapy, prior to balloon deflation.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 8 is a perspective view of a yet further alternative embodiment of a neurotoxin applicator assembly of the present invention;

FIGS. 9A and 9B are partial cross-sectional views of the neurotoxin applicator assembly of FIG. 8 in retracted and extended positions, respectively. FIG. 9AA is a cross-sectional view taken along line 9AA-9AA in FIG. 9A.

DETAILED DESCRIPTION OF THE INVENTION

Figure 1:
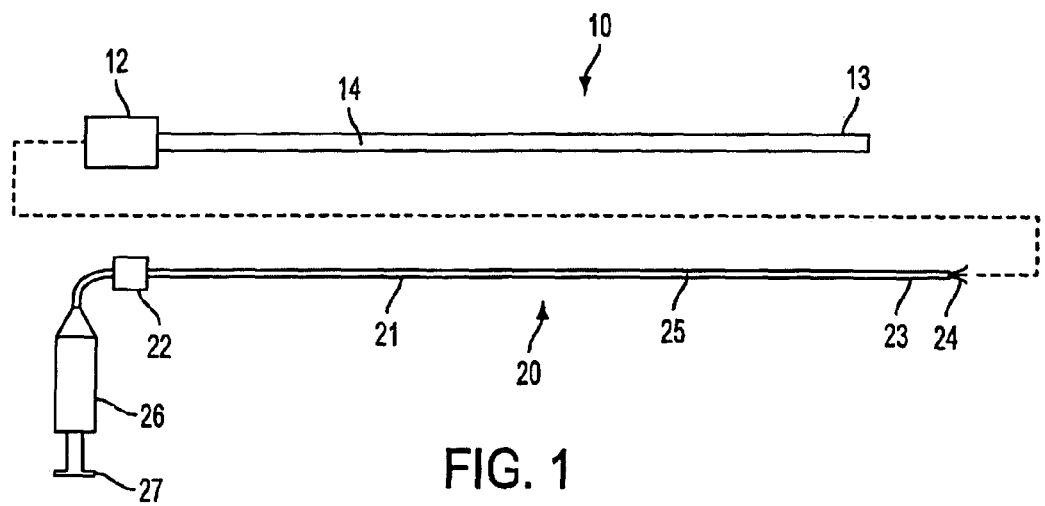
FIG. 1 is a side view of an intrabronchial neurotoxin delivery system of the present invention.

Referring to FIG. 1, apparatus for controlled delivery of neurotoxin to a target treatment area within a patient's bronchial airways to lessen the effects of asthma is described. Preferably, the apparatus comprises bronchoscope 10 and neurotoxin applicator assembly 20. Bronchoscope 10 has proximal end 12, distal end 13, and lumen 14. As is conventional, bronchoscope 10 also includes a light source for illuminating the interior of a patient's lung and optics, such as a miniature camera, that enables the physician to view the interior of the patient's lung. Alternatively, bronchoscope 10 may omit the light source and optics, and instead comprise an outer sheath. In this latter case, device 10 and neurotoxin applicator 20 would be observed using a separate conventional bronchoscope.

In accordance with the principles of the present invention, neurotoxin applicator assembly 20, of which various illustrative embodiments are described hereinbelow, enables the physician to selectively administer controlled doses of neurotoxin to or within selected treatment sites in the patient's lung. More specifically, neurotoxin applicator assembly 20 may be selectively advanced through lumen 14 of bronchoscope 10 to deliver a neurotoxin, such as botulinum toxin, serotype A, to a target treatment area.

Neurotoxin applicator assembly 20 includes shaft 21 coupled to at its proximal end to handle 22, distal end 23 having neurotoxin applicator 24, and lumen 25. Lumen 25 provides fluid communication between proximal end and handle 22 and applicator 24. Syringe 26 having plunger 27 is coupled to a port on proximal end 22. Syringe 26 is filled with neurotoxin in liquid form, and applies the neurotoxin to applicator 24 via lumen 25 when plunger 27 is actuated.

Handle 22 enables the physician to extend and retract applicator 24 from within lumen 14 of bronchoscope 10, and to manipulate distal end 23 of neurotoxin applicator assembly 20 under direct visual observation using the optics of bronchoscope 10. The neurotoxin applicator assembly preferably remains retracted within lumen 14 of the bronchoscope during insertion of the catheter into the patient's bronchial airways, and is deployed once the applicator is in a desired position. Alternatively, applicator 20 may be housed inside of a retaining sheath, and both units can be advanced through lumen 14 together.

Figure 2:
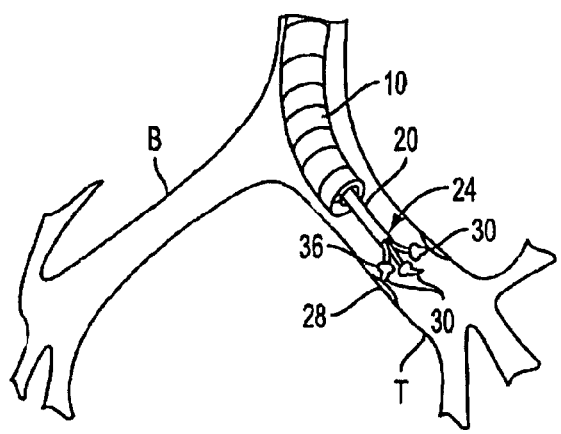
FIG. 2 is a perspective view of an illustrative embodiment of a neurotoxin applicator assembly of the present invention.

Referring now to FIGS. 2-3, a first illustrative embodiment of applicator 24 of neurotoxin applicator assembly 20 constructed in accordance with the principles of the present invention is described. Applicator 241 comprises needle assembly 28 having at least one needle 30 with lumen 31 in fluid communication with lumen 25. The needles are configured to penetrate the airway epithelium and directly inject small amounts of neurotoxin from the syringe into the collagenous and smooth muscle layers of bronchial wall B.

Figure 3A:
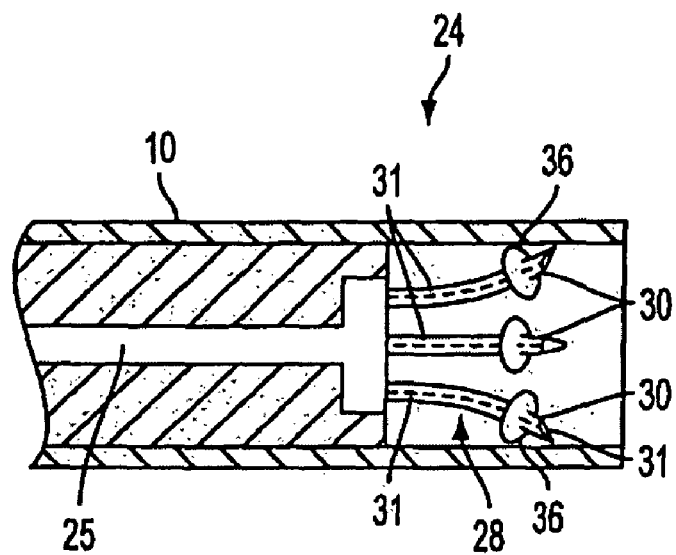
FIGS. 3A and 3B are cross-sectional views of the neurotoxin applicator assembly of FIG. 2 in retracted and extended positions, respectively.
Figure 3B:
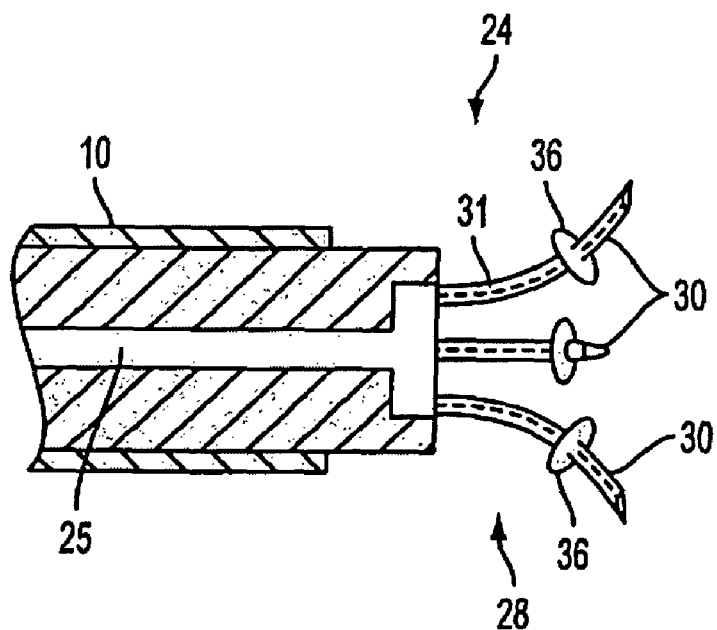

In FIG. 3A, needle assembly 28 is depicted 10 retracted with lumen 14 of bronchoscope 10. Alternatively, device 10 may comprise an outer sheath that is dimensioned to be slidably accept neurotoxin applicator assembly 20, and which is selectively retractable to expose needle assembly 28. In a further embodiment, a retaining sheath housed within lumen 14 and covering applicator 20 is selectably retractable to expose needle assembly 28. As depicted in FIG. 3B, needles 30 comprise a material capable of retaining a preformed shape, such as nickel-titanium, and are preformed to deflect radially outward when extended beyond distal end 13 of bronchoscope 10 (or the distal end of the outer sheath, if present). Each needle 30 optionally includes hilt 36 disposed a pre-selected distance from the distal end of the needle to control the depth of penetration of the needle tip into the bronchial wall.

When needle assembly 30 is deployed, as illustrated in FIGS. 2 and 3B, needles 30 penetrate target treatment area T of bronchial wall B so that neurotoxin may be injected in the bronchial wall. Syringe 26 may include graduations that enable the physician to inject a pre-determined amount of neurotoxin at each target treatment area.

Figure 4:
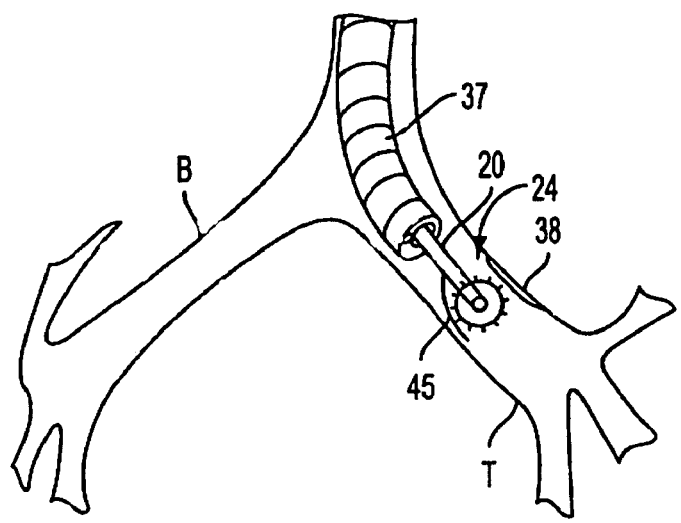
FIG. 4 is a perspective view of an alternative embodiment of a neurotoxin applicator assembly of the present invention.

Referring now to FIGS. 4 and 5, an alternative embodiment of applicator 24 of neurotoxin applicator assembly 20 is described. Applicator 24 in this embodiment comprises rotating needle assembly 38, including wheel 39 mounted to rotate about hub 40. While wheel 39 illustratively is round, it alternatively may comprise a ellipse or hexagon or other polygonal shape. Plurality of needles 41 is disposed around the circumference of the wheel, each needle 41 having lumen 42 in fluid communication with lumen 25 via a passageway in hub 40. Optional fender 45 protects a portion of the bronchial wall substantially opposite the target treatment area.

Figure 5A:
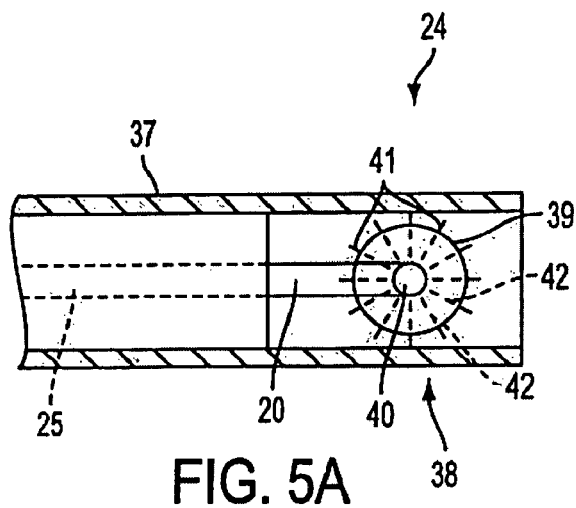
FIGS. 5A and 5B are partial cross-sectional views of the neurotoxin applicator assembly of FIG. 4 in retracted and extended positions, respectively.
Figure 5B:
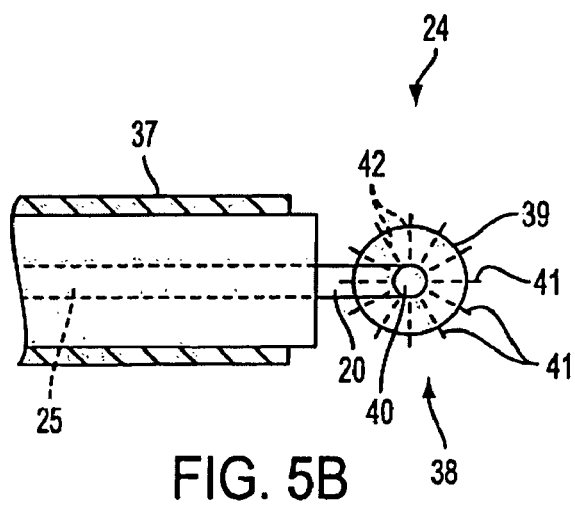

In FIG. 5A, rotating needle assembly 38 is shown retracted within outer sheath 37. Outer sheath 37 is dimensioned to fit within lumen 14 of bronchoscope 10, and may be selectively retracted to expose rotating needle assembly 38. Alternatively, rotating needle assembly 38 extends through lumen 14 and past the tip of bronchoscope 10. In this embodiment, the wheel is covered by a retractable protection sheath which covers the wheel during insertion of, the system. In FIGS. 4 and 5B, rotating needle assembly 38 is shown in the extended position. When so deployed, wheel 39 may be rolled across target treatment area T, so that as the wheel rotates needles 41 alternately penetrate and inject neurotoxin into bronchial wall B.

Suitable needles materials for needle assembly 28 of FIGS. 2-3 and rotating needle assembly 38 of FIGS. 4-5 include shape memory alloys such as nickel titanium alloys and spring tempered stainless steel alloys. Advantageously, either needle assembly permits direct injection of neurotoxin into the bronchial wall. This prevents the cilial transport system from trapping the neurotoxin and transporting it to other regions of the respiratory system, e.g., the oropharynx, where potentially unintended targets may be exposed to the neurotoxin, and prevents accidental exhalation of aerosolized neurotoxin.

Figure 6:
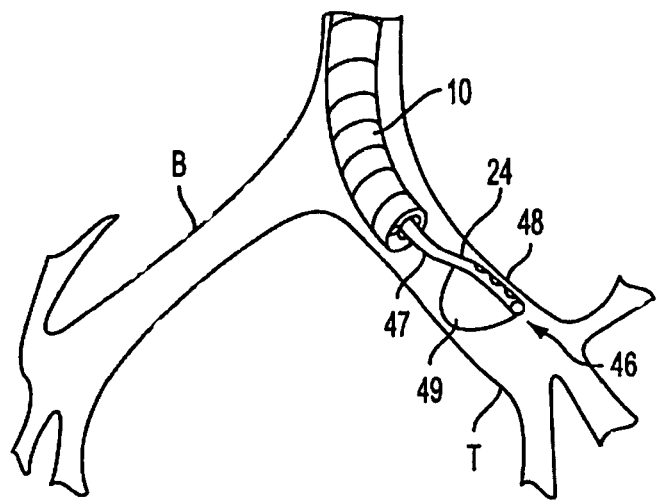
FIG. 6 is a perspective view of another alternative embodiment of a neurotoxin applicator assembly of the present invention.

Referring now to FIGS. 6 and 7, another. alternative embodiment of applicator 24 of the neurotoxin applicator assembly of the present invention is described. Applicator 24 of FIGS. 6-7 comprises a needle-less injection assembly 46, which uses pressurized injection to deliver neurotoxin from the proximal controller to target treatment area T. Advantageously, the needle-less injection assembly allows controlled introduction of neurotoxin across the airway epithelium without the potential complications of introducing needles proximate to the delicate bronchial tissues, and may allow a lower profile system.

Needle-less injection assembly 46 comprises shaft 47 including at least one port 48 in fluid communication with lumen 25. Inflatable balloon 49 optionally may be coupled to shaft 47, and used to position the shaft adjacent target treatment area T. Balloon 49 is inflated with a fluid introduced through a lumen of shaft 47. When the shaft is aligned with the target treatment area, pulses of pressurized gas may be employed to inject predetermined amounts of neurotoxin across the airway wall and into the collagenous and smooth muscle layers.

Figure 7A:
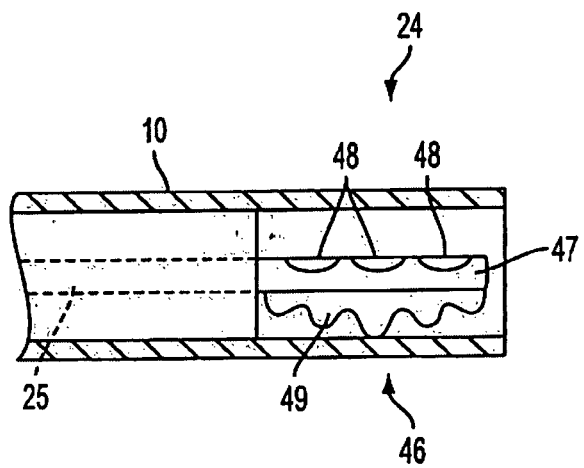
FIGS. 7A and 7B are partial cross-sectional views of the neurotoxin applicator assembly of FIG. 6 in retracted and extended positions, respectively.
Figure 7B:
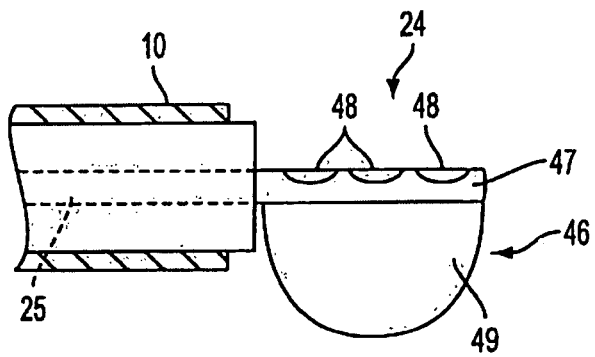

In FIG. 7A, needle-less injection assembly 46, with balloon 49 deflated, is depicted housed within the lumen 14 of bronchoscope 10 (or a separate outer sheath). FIGS. 6 and 7B depict needle-less injection assembly 46 with balloon 49 inflated to place ports 48 in apposition to target treatment area T. Once the physician has confirmed placement of needle-less injection assembly 46, e.g., by visualization using the optics of bronchoscope 10, x-ray, fluoroscopy or other suitable means, a controller attached to the proximal end of neurotoxin applicator assembly 20 (instead of syringe 26), may be activated to deliver the desired doses of neurotoxin to the bronchial wall. As an alternative to the balloon 49, the assembly may have 2 or more needle-less injectors arranged to position against opposite walls of the bronchial passage. For instance, they might be spring loaded to expand the sections away from the midline and contact the bronchial wall. As a further alternative, the shaft of the assembly may be pre-curved or actively curved with an activation mechanism to urge the injector against the wall of the bronchial passage.

With respect to FIGS. 8 and 9, a yet further alternative embodiment of applicator 24 of the neurotoxin applicator assembly constructed in accordance with the present invention is described. Applicator 24 comprises nebulizer assembly 50 having shaft 55 with atomizer 51 disposed at its distal end and in fluid communication with central lumen 25. Atomizer 51 converts the liquid neurotoxin from the syringe into a fine spray or mist. Particle size of the mist can be controlled through nebulizer head design or by varying injection pressure in order to control the depth of penetration of the mist into the target segment.

Nebulizer assembly 50 may also include optional inflatable balloon 52 disposed on shaft 55 proximal of atomizer 51. Selective inflation of balloon 52 allows positioning of atomizer 51 so that aerosolized neurotoxin may be directly sprayed onto target treatment area T. Balloon 52 also acts to isolate the treatment area from the rest of the lung, preventing reflux of mist into unintended areas. As for the embodiment of FIGS. 6-7, balloon 52' may be inflated using a fluid introduced through an auxiliary lumen in shaft 55.

In FIG. 9A, the nebulizer assembly, including deflated balloon 52, is disposed within lumen 14 of bronchoscope 10, or alternatively, in an outer sheath (not shown) that is slidably received in lumen 14. Alternatively, the nebulizer assembly 50 may be inserted within a separate delivery sheath (not shown), with the bronchoscope 10 inserted separately. In FIGS. 8 and 9B, nebulizer assembly 50 is depicted deployed from lumen 14 (or the outer sheath, if present), with balloon 52 on shaft 55 inflated. Advantageously, nebulizer assembly 50 can be dimensioned to access very small bronchial passageways, and also may be used to deliver neurotoxin to upstream regions of the lung.

Still referring to FIGS. 9A and 9B, shaft 55 which carries balloon 52 may optionally also include an additional auxiliary lumen or lumens 25a, 25b (FIG. 9AA) coupled to inlet port 53 and outlet port 54 disposed between the balloon 52 and the atomizer 51. Lumen 25 provides for medicine delivery as in previous embodiments. Inlet port 53 allows the introduction of gas (such as fresh air) near the target treatment area, while outlet port 54 allows air or gas mixed with atomized neurotoxin to be removed. Inlet and outlet ports 53 and 54 therefore provide a ventilation system that shields tissue adjacent and proximal to target treatment area T from being inadvertently exposed to the atomized neurotoxin. Inlet and outlet ports 53 and 54 further serve to either actively inflate and deflate the isolated segment, or simply to normalize pressure within the lung near the target treatment area. The lumens 25, 25a, and 25b may be connected to the neurotoxin source, gas source, and an aspiration source via ports 23a, 23b, and 23c in handle 22. A control unit may be connected to the proximal outlets of ports 53 and 54 to control the introduction and removal of gases from the lung without allowing escape of atomized neurotoxin to the environment or patient.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A method for treating the bronchial airways of a patient, said method comprising:
    endobronchially positioning a shaft at a location in a bronchial airway, the shaft having a plurality of needles coupled near a distal end thereof;
    penetrating at least one needle from the shaft across an epithelium and a mucosa of the bronchial airway;
    positioning at least a portion of the at least one needle at a treatment site outside of the mucosa, the treatment site including at least one of a smooth muscle layer of the bronchial airway and a collagenous layer of the bronchial airway; and
    delivering a medication out of the at least one needle to nerve tissue at the treatment site so as to inhibit hyperresponsiveness of smooth muscle cells in the bronchial tissue while inhibiting transport of the delivered medication away from the treatment site to non-targeted tissue outside the bronchial airway.

2. The method as in claim 1, wherein the medication lessens the effects of asthma.

3. The method as in claim 2, wherein the medication comprises a neurotoxin.

4. The method of claim 3, wherein the neurotoxin comprises botulinum toxin, serotype A.

5. The method of claim 3, wherein the neurotoxin comprises botulinum toxin, serotype B.

6. The method of claim 1, wherein penetrating comprises advancing at least one needle from the shaft.

7. The method of claim 1, wherein penetrating comprises rotating a needle-bearing wheel over a wall of the bronchial airway, and injecting comprises injecting the medication through a plurality of needles in the wheel.

8. The method of claim 1, wherein penetrating and injecting comprises penetrating and injecting with a plurality of needles.

9. The method of claim 1, further comprising:
    positioning an end of the at least one needle a pre-selected distance from a lumen of the bronchial airway using an injection stop, the pre-selected distance corresponding to a distance between the lumen and nerve tissue that transmits signals to the smooth muscle cells.

10. The method of claim 9, wherein positioning the end of the at least one needle comprises contacting the bronchial tissue with the injection stop, the injection stop comprising at least one of a hilt carried by the at least one needle and a wheel from which the plurality of the needles extend.

11. The method of claim 1, further comprising:
    contacting the bronchial tissue of the bronchial airway with a hilt carried by the at least one needle or a wheel from which the plurality of needles extend to position an end of the at least one needle at the treatment site.

12. The method of claim 1, further comprising:
    keeping an end of the at least one needle located in smooth muscle tissue of the bronchial airway while the medication is delivered out of the end of the at least one needle.

13. A method of treating a subject, comprising:
    moving a shaft along a bronchial passageway defined by a bronchial wall, the shaft is coupled to a medication applicator including a needle assembly having at least one needle and a penetration stop, the penetration stop spaced apart from an end of the at least one needle a distance corresponding to a distance between the bronchial passageway and a nerve tissue treatment site, the nerve tissue treatment site being disposed outside a mucosal layer and being located in a smooth muscle layer of the bronchial wall or a collagenous layer of the bronchial wall;
    moving the at least one needle through the mucosal layer to position the end of the at least one needle proximate to the nerve tissue treatment site; and
    delivering medication through the at least one needle to the nerve tissue treatment site so as to inhibit hyperresponsiveness of the bronchial wall while the medication is inhibited from being transported away from the nerve tissue treatment site.

14. The method of claim 13, further comprising:
    contacting the bronchial wall with the penetration stop to inhibit movement of the at least one needle into the bronchial wall.

15. The method of claim 14, wherein contacting the bronchial wall with the penetration stop includes moving the penetration stop in the form of a hilt coupled to the at least one needle against the bronchial wall.

16. The method of claim 13, further comprising:
    moving the medication applicator from a delivery configuration to a deployed configuration to move a plurality of needles into an injection position, the plurality of needles including the at least one needle; and
    penetrating the bronchial wall with the plurality of needles.

17. The method of claim 13, wherein moving the at least one needle through the mucosa and collagenous layer comprises moving a tip of the at least one needle outwardly past at least a portion of the collagenous layer towards nerve tissue that transmits signals to smooth muscle tissue of the bronchial wall.

18. A method of treating a subject, comprising:

moving a bronchoscope along a bronchial passageway;

moving a medication applicator of an apparatus out of the bronchoscope;

moving the medication applicator from a delivery position to a deployed position such that a plurality of needles extend radially outward from a shaft of the apparatus, the medication applicator is coupled to the shaft;

penetrating a bronchial wall with the plurality of needles; and delivering medication through at least one of the plurality of needles extending through a mucosal lager along the bronchial passageway to directly deliver the medication to a target site that comprises at least one of a collagenous layer and a smooth muscle layer such that the delivered medication at the target site inhibits hyperresponsiveness of the bronchial wall and is inhibited from moving to non-targeted tissue.

19. The method of claim 18, further comprising:

positioning an end of the at least one needle adjacent to nerve tissue of the target site to deliver the medication towards the nerve tissue that delivers signals to smooth muscle layer in the bronchial wall.

20. The method of claim 1, wherein the medication is delivered out of the at least one needle such that the medication is directly delivered to the treatment site to affect the nerve tissue while protecting the mucosa from the medication.

21. The method of claim 13, wherein delivering the medication includes directly delivering the medication to the nerve tissue treatment site while inhibiting transport of the medication to the mucosal layer, and the nerve tissue treatment site comprises nerve tissue that causes hyperresponsiveness of the bronchial wall.

22. The method of claim 18, wherein delivering the medication further comprising directly delivering the medication to the target site to inhibit transport of the delivered medication to the mucosal layer.

\* \* \* \* \*

UNITED STATES PATENT AND TRADEMARK OFFICE
CERTIFICATE OF CORRECTION

| | | |
|---|---|---|
| PATENT NO. | : 8,172,827 B2 | Page 1 of 1 |
| APPLICATION NO. | : 11/445644 | |
| DATED | : May 8, 2012 | |
| INVENTOR(S) | : Mark E. Deem et al. | |

It is certified that error appears in the above-identified patent and that said Letters Patent is hereby corrected as shown below:

Column 9, Line 11:
"plurality of needles extending through a mucosal lager" should read, --plurality of needles extending through a mucosal layer--.

Signed and Sealed this
Eighteenth Day of December, 2012

David J. Kappos
*Director of the United States Patent and Trademark Office*